(12) United States Patent
Gebrian

(10) Patent No.: US 10,272,574 B2
(45) Date of Patent: Apr. 30, 2019

(54) ROBOTIC PICK AND PLACE DEVICE WITH COMBINED GRIPPING AND ROTATIONAL FUNCTIONALITY

(71) Applicant: Siemens Healthcare Diagnostics Inc., Tarrytown, NY (US)

(72) Inventor: Peter Gebrian, Townsend, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 217 days.

(21) Appl. No.: 15/127,339

(22) PCT Filed: Apr. 1, 2015

(86) PCT No.: PCT/US2015/023881
§ 371 (c)(1),
(2) Date: Sep. 19, 2016

(87) PCT Pub. No.: WO2015/153759
PCT Pub. Date: Oct. 8, 2015

(65) Prior Publication Data
US 2017/0173801 A1    Jun. 22, 2017

Related U.S. Application Data

(60) Provisional application No. 61/975,203, filed on Apr. 4, 2014.

(51) Int. Cl.
*B25J 15/02* (2006.01)
*G01N 35/00* (2006.01)

(52) U.S. Cl.
CPC ........ *B25J 15/026* (2013.01); *G01N 35/0099* (2013.01); *G01N 2035/00326* (2013.01)

(58) Field of Classification Search
CPC ................. B25J 15/026; G01N 35/009; G01N 2035/00326
See application file for complete search history.

(56) References Cited

U.S. PATENT DOCUMENTS

| 4,600,357 A | 7/1986 | Coules |
| 4,918,991 A | 4/1990 | Bucher et al. |

(Continued)

FOREIGN PATENT DOCUMENTS

| EP | 0 993 916 A2 | 4/2000 |
| JP | 2012-81564 A | 4/2012 |

(Continued)

OTHER PUBLICATIONS

PCT International Search Report and Written Opinion dated Jul. 8, 2015 (11 Pages).

(Continued)

*Primary Examiner* — Benjamin R Whatley

(57) ABSTRACT

A pick and place device for use in an in vitro diagnostics automation system is provided that includes a motor and a rotatable motor shaft coupled to the motor and a gripping assembly. The gripping assembly includes a yoke selectively coupled to the rotatable motor shaft and configured to rotate with the rotatable motor shaft when the yoke is coupled to the rotatable motor shaft. The gripping assembly also includes a first movable finger mount and a second movable finger mount each coupled to the rotatable motor shaft and configured to move toward each other and away from each other in a linear direction responsive to the rotation of the motor shaft when the yoke is uncoupled from the rotatable motor shaft. Fingers extending from the movable finger mounts are configured to move toward each other and away from each other in the linear direction and rotate with the yoke.

19 Claims, 21 Drawing Sheets

(56) References Cited

U.S. PATENT DOCUMENTS

| | | |
|---|---|---|
| 5,046,773 A | 9/1991 | Modesitt |
| 6,116,670 A | 9/2000 | Palone et al. |
| 6,520,313 B1 | 2/2003 | Kaarakainen et al. |
| 2005/0013737 A1 | 1/2005 | Chow et al. |
| 2009/0047179 A1* | 2/2009 | Ping .................. G01N 35/0095 422/72 |
| 2009/0087343 A1* | 4/2009 | Meinicke ................ B25J 15/00 422/64 |
| 2012/0088293 A1* | 4/2012 | Hamada ............... G01N 35/026 435/287.1 |
| 2013/0019697 A1* | 1/2013 | McKeen ................ G01N 1/312 73/863.21 |

FOREIGN PATENT DOCUMENTS

| | | |
|---|---|---|
| KR | 10-2014-0022172 A | 2/2014 |
| WO | 2013/116669 A1 | 8/2012 |

OTHER PUBLICATIONS

Extended EP Search Report dated Mar. 9, 2017 of corresponding European Application No. 15772678.7, 4 Pages.

* cited by examiner

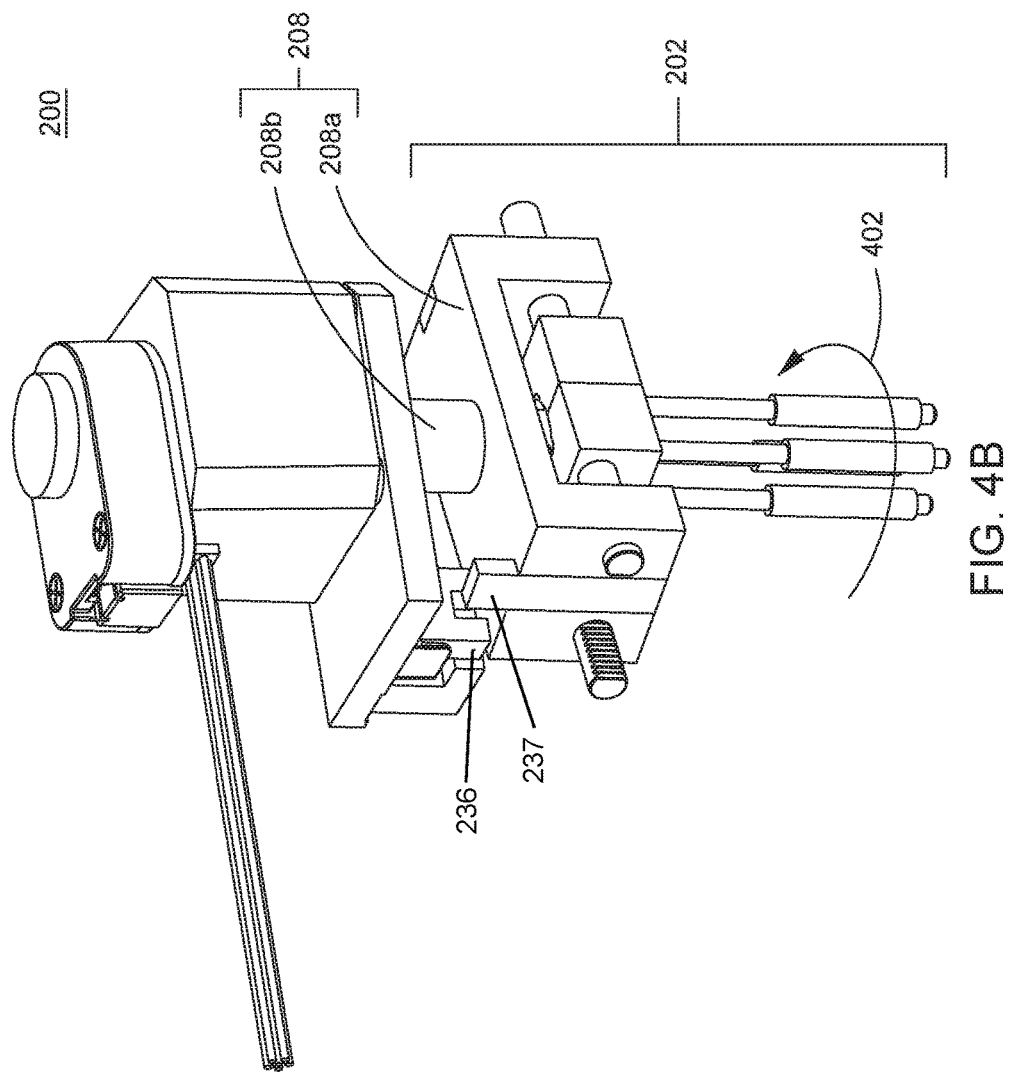

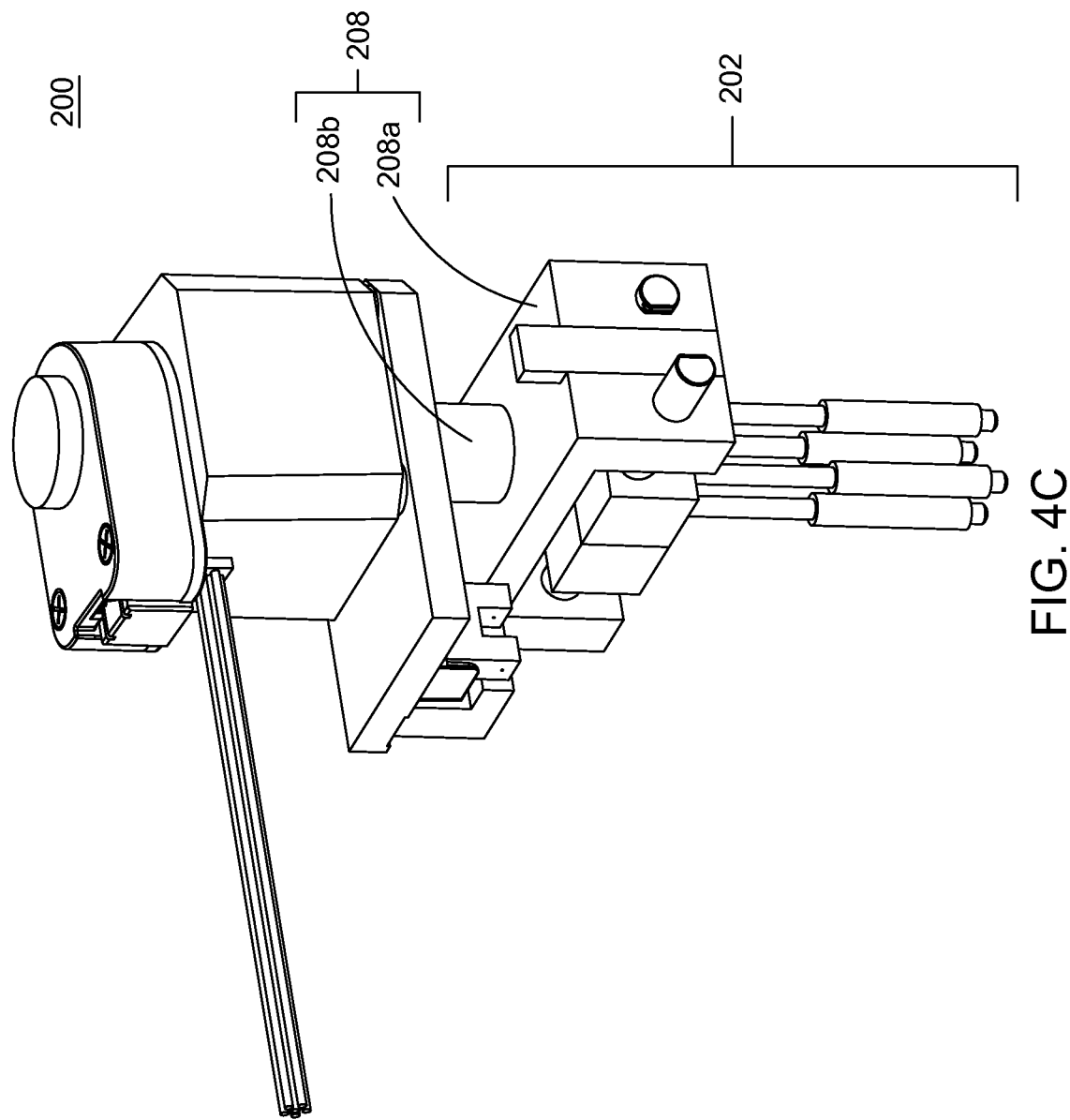

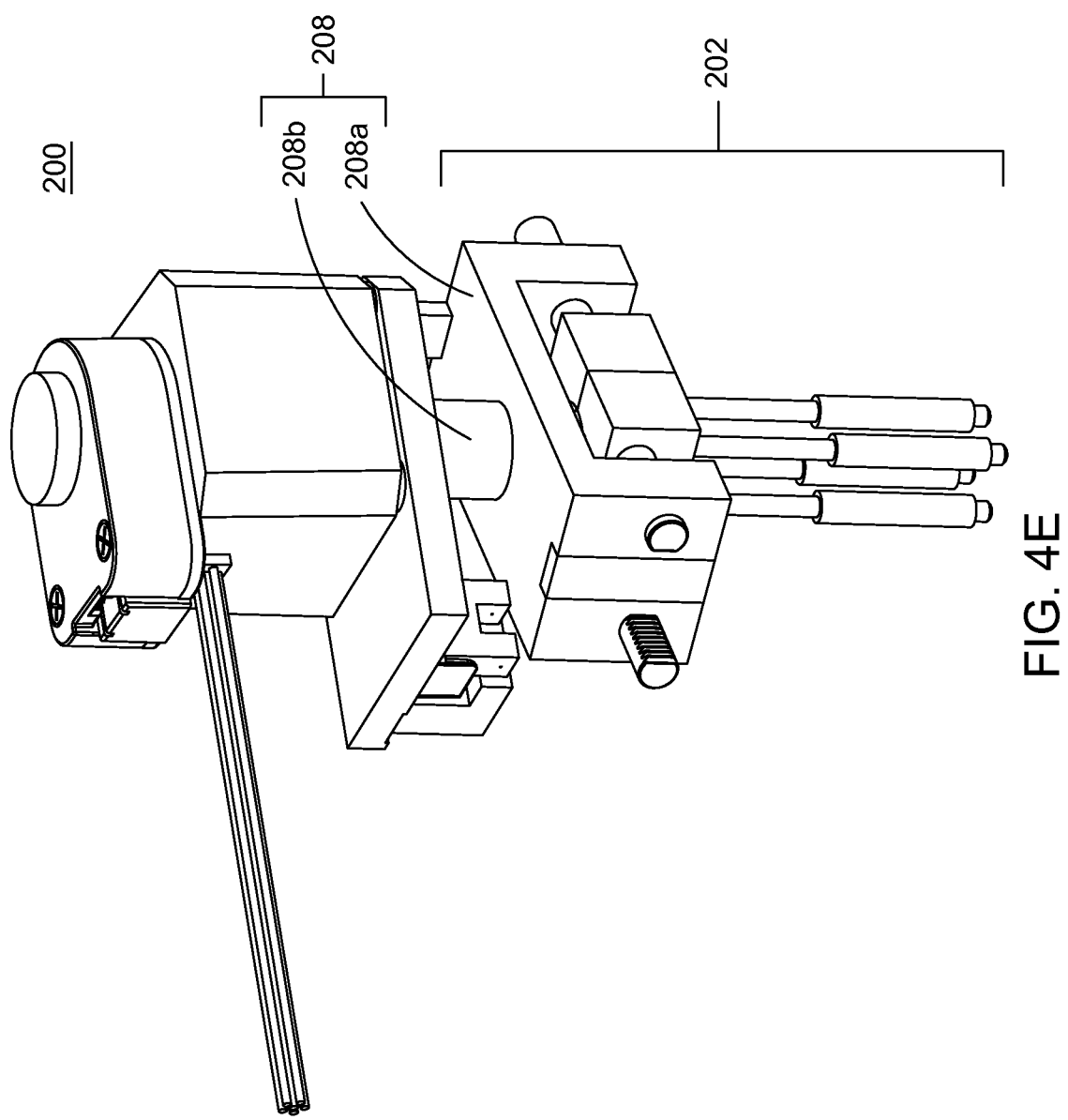

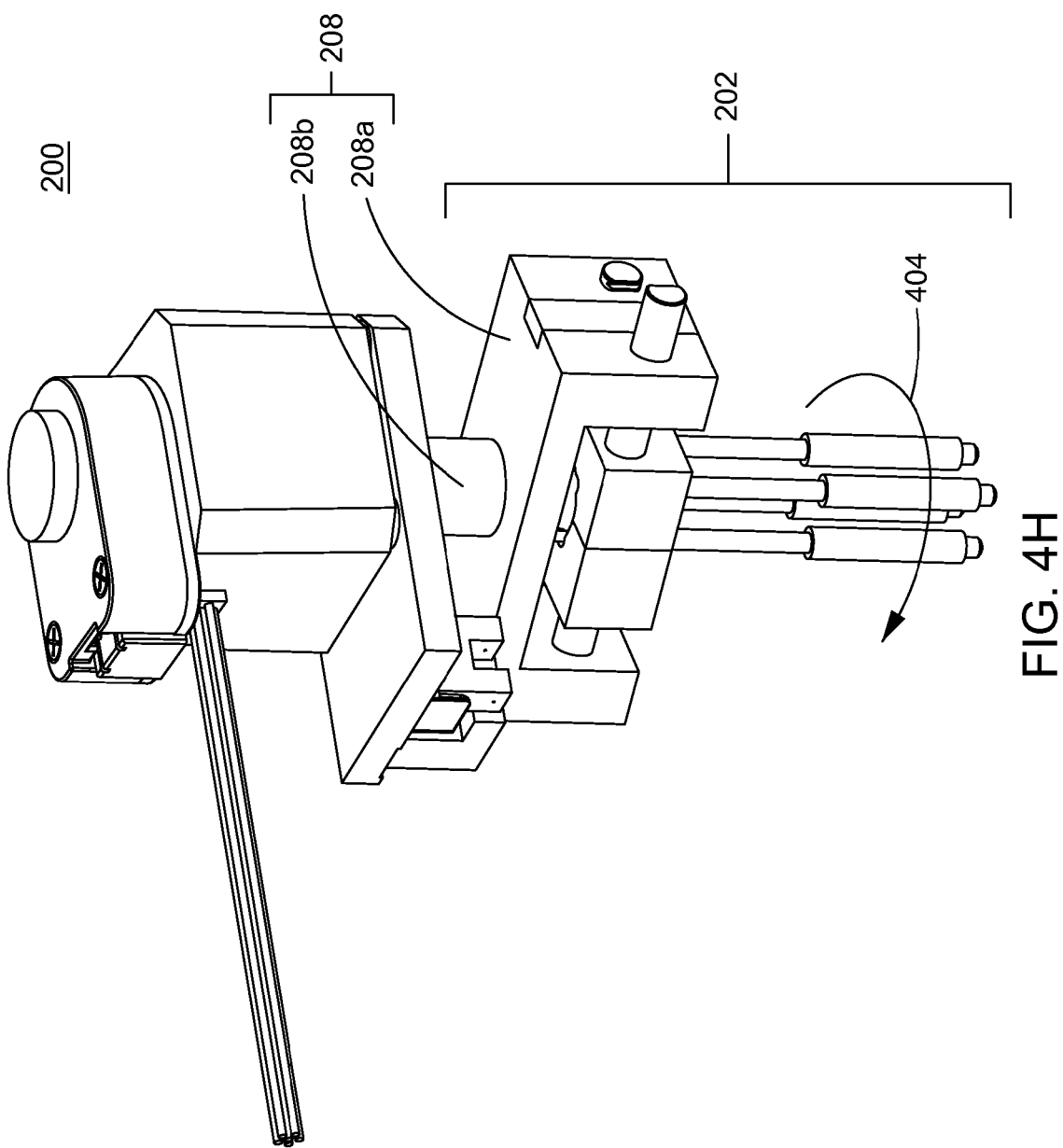

ROBOTIC PICK AND PLACE DEVICE WITH COMBINED GRIPPING AND ROTATIONAL FUNCTIONALITY

CROSS REFERENCE TO RELATED APPLICATIONS

This application claims priority to U.S. provisional application Ser. No. 61/975,203 filed Apr. 4, 2014, which is incorporated herein by reference in its entirety.

TECHNOLOGY FIELD

The embodiments disclosed herein relate in general to a pick and place device that provides gripping and rotational functionality and, in particular, to an automated pick and place device that combines gripping and rotational functionality to transfer and orient items in a clinical diagnostics automation system.

BACKGROUND

In vitro diagnostics (IVD) allows labs to assist in the diagnosis of disease based on assays performed on patient fluid samples. IVD includes various types of analytical tests and assays typically conducted with automated clinical chemistry analyzers (analyzers) onto which fluid containers, such as tubes or vials containing patient samples (e.g., blood samples), have been loaded. The analyzer extracts a fluid sample from the vial and combines the sample with various reagent fluids (reagents) in special reaction cuvettes or tubes (referred to generally as reaction vessels).

Some conventional automation systems include automated pick and place devices, sometimes referred to as robotic grippers or end effectors, which are used to grip items (e.g., fluid containers and reaction vessels) to perform automated pick and place operations to transfer the items between one location of the analyzer to another location of the analyzer for subsequent processing. These items are also typically reoriented during the transfer operation. For example, an item may be rotated to present an item indicator (e.g., bar code label) to an item identifier (e.g., scanner) during operation to determine or confirm identification of the item and facilitate performance of ordered tests and reporting results of the tests.

SUMMARY

Embodiments provide a pick and place device for use in an in vitro diagnostics automation system. The pick and place device includes a single motor and a rotatable motor shaft coupled to the single motor. The pick and place device also includes a gripping assembly. The gripping assembly includes a yoke selectively coupled to the rotatable motor shaft and configured to rotate with the rotatable motor shaft when the yoke is coupled to the rotatable motor shaft. The gripping assembly also includes a first movable finger mount and a second movable finger mount each coupled to the rotatable motor shaft and configured to move toward each other and away from each other in a linear direction responsive to the rotation of the motor shaft when the yoke is uncoupled from the rotatable motor shaft. The gripping assembly also includes a first set of fingers extending from the first movable finger mount and configured to: (i) move in the linear direction with the first movable finger mount when the yoke is uncoupled from the rotatable motor shaft; and (ii) rotate with the yoke when the yoke is coupled to the rotatable motor shaft. The gripping assembly further includes a second set of fingers extending from the second movable finger mount and configured to: (i) move in the linear direction with the second movable finger mount when the yoke is uncoupled from the rotatable motor shaft; and (ii) rotate with the yoke when the yoke is coupled to the rotatable motor shaft.

According to an embodiment, the pick and place device further includes a pinion coupled to the rotatable motor shaft and configured to rotate with the rotatable motor shaft. The pick and place device further includes a first movable rack gear connected to the first movable finger mount and movably coupled to the pinion and configured to move the first movable finger mount in the linear direction when the pinion rotates. The pick and place device further includes a second movable rack gear connected to the second movable finger mount and movably coupled to the pinion and configured to move the second movable finger mount in the linear direction when the pinion rotates.

According to another embodiment, the pick and place device further includes an encoder configured to generate a number of pulses per revolution of the gripping assembly when the encoder is moving with the rotatable motor shaft, a home sensor configured to emit a beam and a home flag configured to block the beam of the home sensor and provide a home position of the gripping assembly.

In one embodiment, the rotatable yoke is further configured to rotate in a clockwise direction and a counter-clockwise direction with the rotatable motor shaft.

In another embodiment, the pick and place device further includes a stopper and a protruding portion extending from the gripper assembly. When the rotatable yoke is rotating in the counter-clockwise direction and the stopper contacts the protruding portion, the rotatable yoke is prevented from further rotating in the counter-clockwise direction. When the rotatable yoke is rotating in the clockwise direction and the stopper contacts the protruding portion, the rotatable yoke is prevented from further rotating in the clockwise direction.

In an aspect of an embodiment, the pick and place device further includes a spring loaded stopper and a protruding portion extending from the gripper assembly. The rotatable yoke is prevented from further rotating in one of the clockwise direction or the counter-clockwise direction when the spring loaded stopper contacts the protruding portion. The rotatable yoke is free to further rotate continuously in the other of the clockwise direction or the counter-clockwise direction.

In another aspect of an embodiment, the pick and place device further includes a one-way motion device configured to prevent the rotatable yoke from rotating in one of the clockwise direction or the counter-clockwise direction.

In yet another embodiment, the pick and place device includes a first spring fixedly coupled between the yoke and the first movable finger mount. The first spring is configured to apply a first inward force to the first movable finger mount toward the second movable finger mount in the linear direction. The pick and place device also includes a second spring fixedly coupled between the yoke and the second movable finger mount. The second spring is configured to apply a second inward force to the second movable finger mount toward the first movable finger mount in the linear direction.

Embodiments provide a pick and place device for use in an in vitro diagnostics automation system. The pick and place device includes a motor and a rotatable motor shaft coupled to the motor and configured to rotate. The pick and place device also includes a gripping assembly. The gripping assembly includes a yoke selectively coupled to the rotatable motor shaft. The gripping assembly also includes a first movable finger mount having a first set of fingers extending therefrom and a second movable finger mount having a second set of fingers extending therefrom. The first movable finger mount and the second movable finger mount are coupled to the rotatable motor shaft. The gripping assembly is configured to switch between: (i) a first state such that the rotation of the motor shaft causes the first movable finger mount and the first set of fingers to move in a linear direction toward and away from the second movable finger mount and the second set of fingers when the yoke is uncoupled from the rotatable motor shaft; and (ii) a second state such that the rotation of the motor shaft causes the yoke, the first movable finger mount, the second movable finger mount, the first set of fingers and the second set of fingers to rotate when the yoke is coupled to the rotatable motor shaft.

Embodiments provide an in vitro diagnostics automation system that includes one or more analyzers, analyzer having a track configured to provide one or more paths between one or more testing stations. The system also includes a plurality of items to be transferred between different locations of the analyzer and one or more pick and place devices. Each of the one or more pick and place devices includes a motor, a rotatable motor shaft coupled to the motor and configured to rotate and a gripping assembly. The gripping assembly includes a yoke selectively coupled to the rotatable motor shaft. The first movable finger mount and the second movable finger mount are coupled to the rotatable motor shaft. The first set of fingers extend from the first movable finger mount and a second set of fingers extend from the second movable finger mount. The gripping assembly is configured to switch between: (i) a first state such that the rotation of the motor shaft causes the first movable finger mount and the first set of fingers to move in a linear direction toward and away from the second movable finger mount and the second set of fingers to grip and release one or more of the plurality of items when the yoke is uncoupled from the rotatable motor shaft; and (ii) a second state such that the rotation of the motor shaft causes the yoke, the first movable finger mount, the second movable finger mount, the first set of fingers and the second set of fingers to rotate in the rotational direction to orient one or more of the plurality of items when the yoke is coupled to the rotatable motor shaft.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following Figures:

FIG. 4A through FIG. 4L are perspective views of the pick and place device at different states of the gripping assembly's rotational motion, according to an embodiment.

DESCRIPTION OF EXEMPLARY EMBODIMENTS

Conventional automated pick and place devices include separate drives for each motion (e.g., rotational motion and gripping motion) or degrees of freedom (axis of motion). Each drive of these conventional pick and place devices typically includes a motor or pneumatic actuator, a position sensor, and a feedback device, such as an encoder, for closed loop position control. Automated pick and place devices having these separate drives, however, have a large overall size, are costly, complex and subject to fatigue failure as the wires or hoses are flexed during each relative move.

Embodiments disclosed herein include pick and place devices having a single motor, a single encoder, and a single home sensor to provide both grip and rotate functions. The pick and place devices include a gripping assembly mounted to a motor shaft and configured to be: (i) in a first state such that the assembly moves linearly to generate a gripping function; and (ii) in a second state of rotating with the motor shaft to generate rotational motion. The rotational motion and gripping motion are provided without any wires or hoses to be flexed, thereby reducing or eliminating potential fatigue failures.

Embodiments of the invention may be used with any application for gripping, rotating and/or reorienting of items in any automation system, such as a clinical diagnostics automation system for transfer and identification of patient sample tubes or specimens. Embodiments of the invention include pick and place devices that transfer items, such as fluid containers and reaction vessel, between one location of the analyzer to another location of the analyzer, such as between system conveyors and diagnostic instruments. For example, pick and place devices include portions configured to move linearly to grip and release the items for transfer between locations. The pick and place devices also include portions configured to rotate to orient the items for different functions, such as presenting an item indicator (e.g., bar code label) to an item identifier (e.g., scanner). Pick and place devices disclosed in embodiments herein may be particularly well suited for, but in no way limited to, IVD environments.

Figure 1:
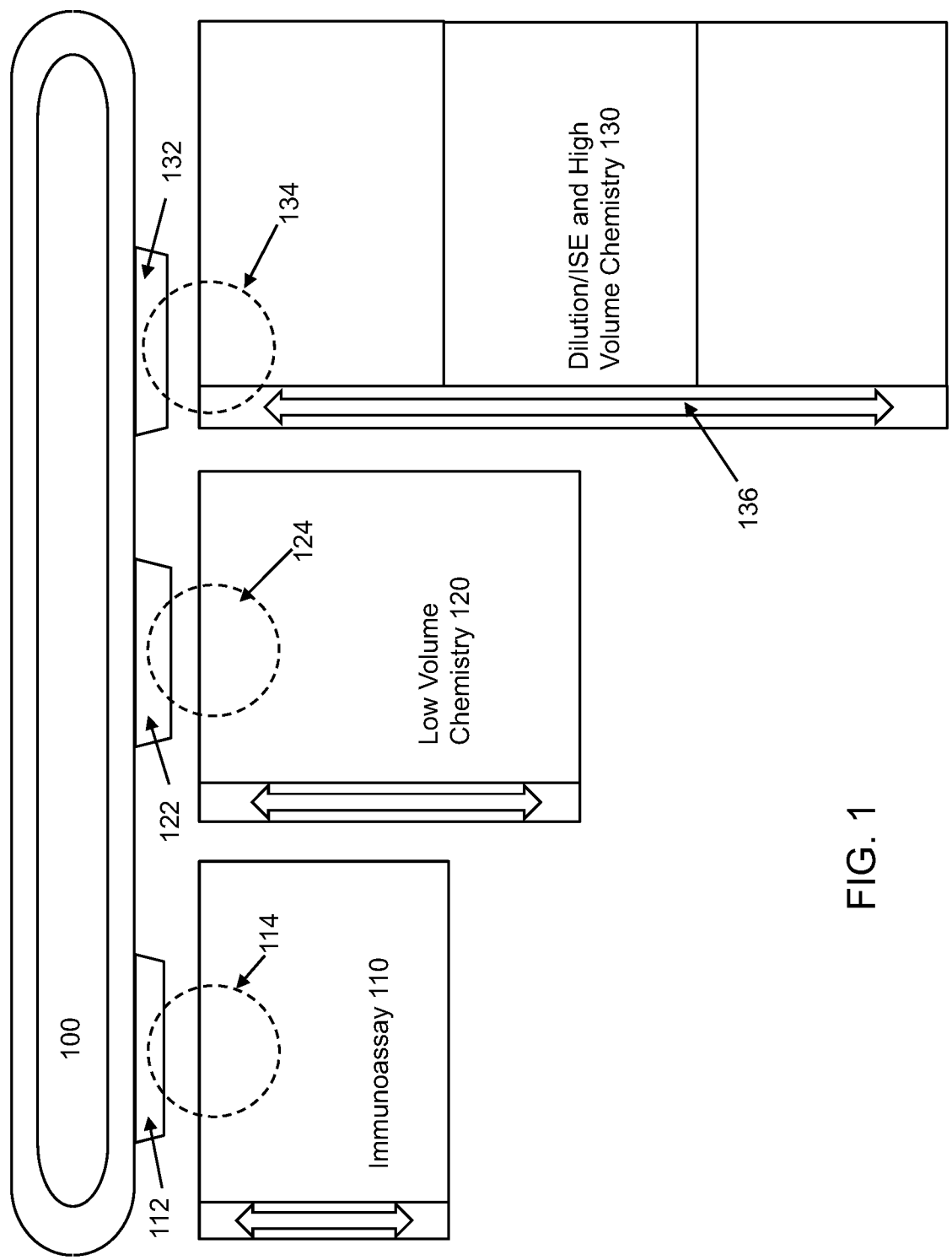
FIG. 1 is a top view of an exemplary clinical analyzer geometry that may be used with embodiments disclosed herein.

An exemplary track geometry for use in transporting items (e.g., fluid containers and reaction vessels) within an analyzer is shown in FIG. 1. Embodiments may include automated systems having more than one analyzer with each analyzer having a track configured to provide one or more paths between one or more testing stations. As used herein, an analyzer can refer to any automated system for preparing or testing properties of patient samples in an automated manner.

Track 100 may be a generally oval-shaped track that conveys items (e.g., in pucks or trays) between various stations, such as sample preparation or analyzing/testing stations 110, 120, and 130. Exemplary tracks may, however, be shaped different from the shape of track 100 shown in FIG. 1. Tracks may be a single direction track or, in some instances, a linear bidirectional track. In the exemplary set-up shown in FIG. 1, each analyzer 110, 120, 130 is serviced by a respective sidecar 112, 122, 132. Embodiments may also include analyzers without sidecars.

Pick and place devices may be used to handle items at different locations in an analyzer. For example, pick and place devices may be located at areas 114, 124, and 134 shown in FIG. 1. Embodiments may include pick and place devices at locations different from the locations of the pick and place devices shown in FIG. 1. These robotic pick and place devices can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Embodiments may include other types of stations and any number of stations. Some stations, such as high-volume chemistry station 130, can include their own friction track 136 that operates independently of track 100. Friction track 136 can include a bidirectional friction track that allows samples to move between sub-modules of high-volume chemistry station 130. Embodiments may, however, include stations without any independent tracks.

Figure 2A:
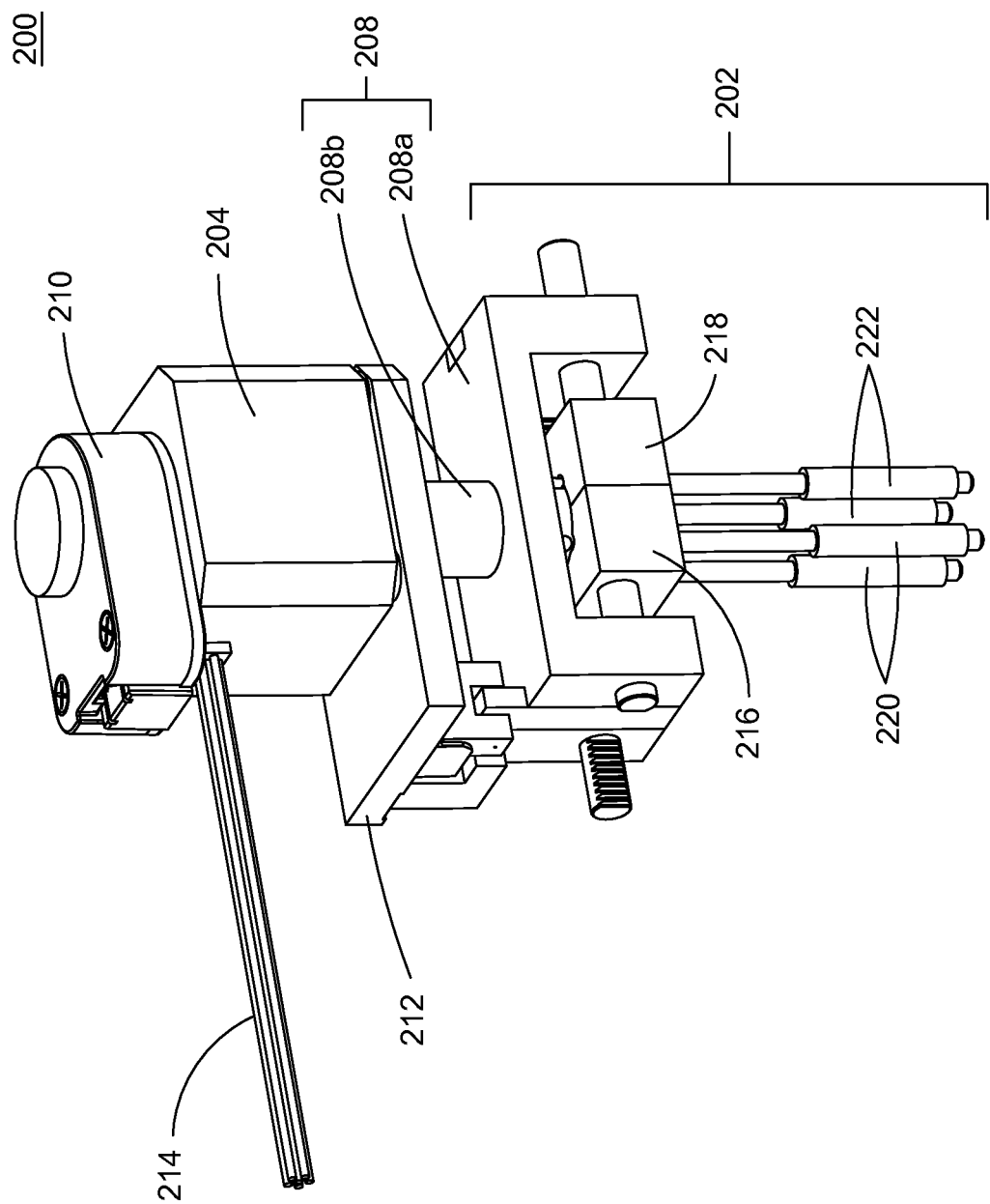
FIG. 2A is a perspective view of an exemplary pick and place device, according to an embodiment.
Figure 2B:
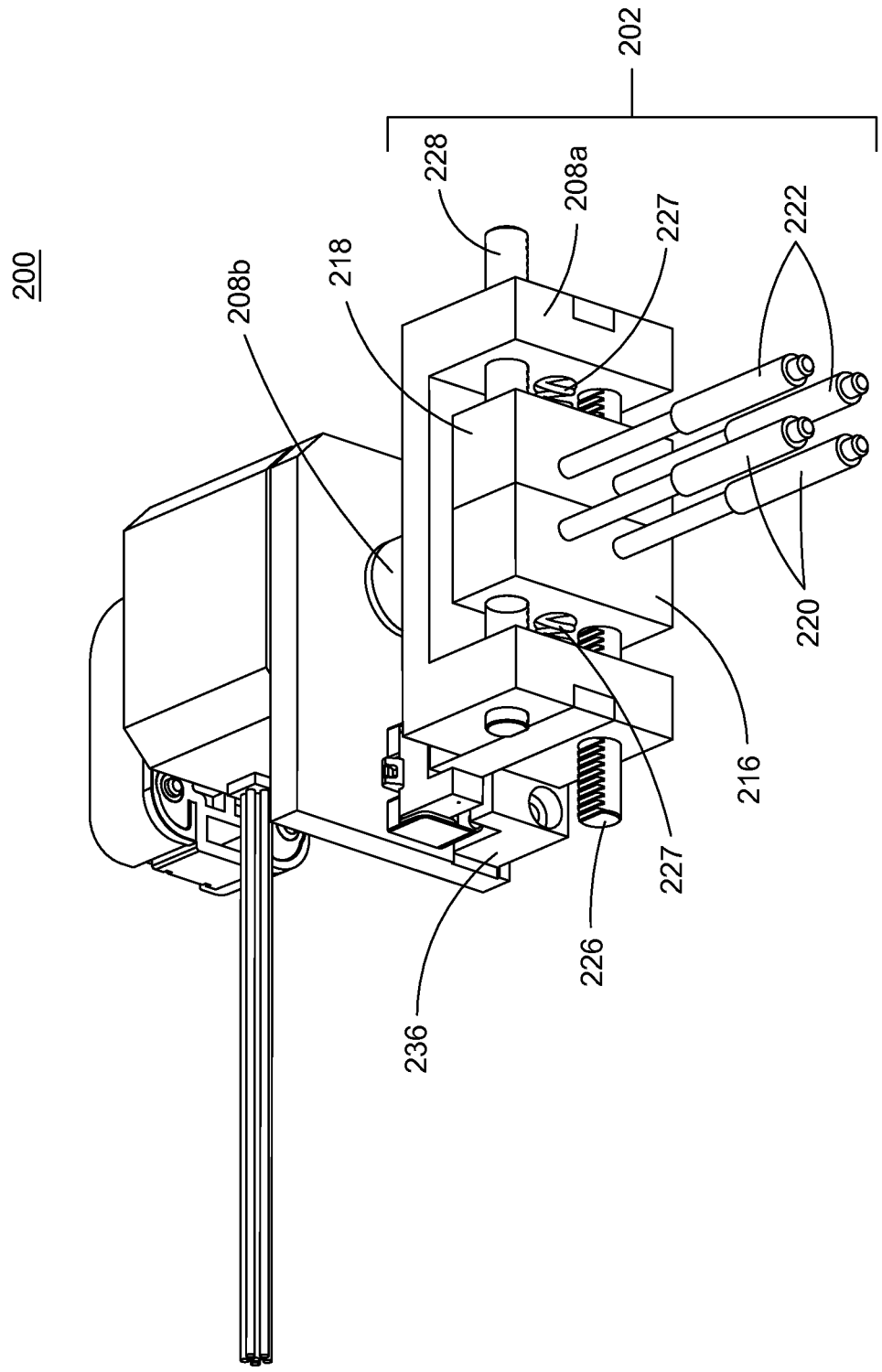
FIG. 2B is a perspective view of the pick and place device shown in FIG. 2A illustrating components of the gripper assembly.
Figure 2C:
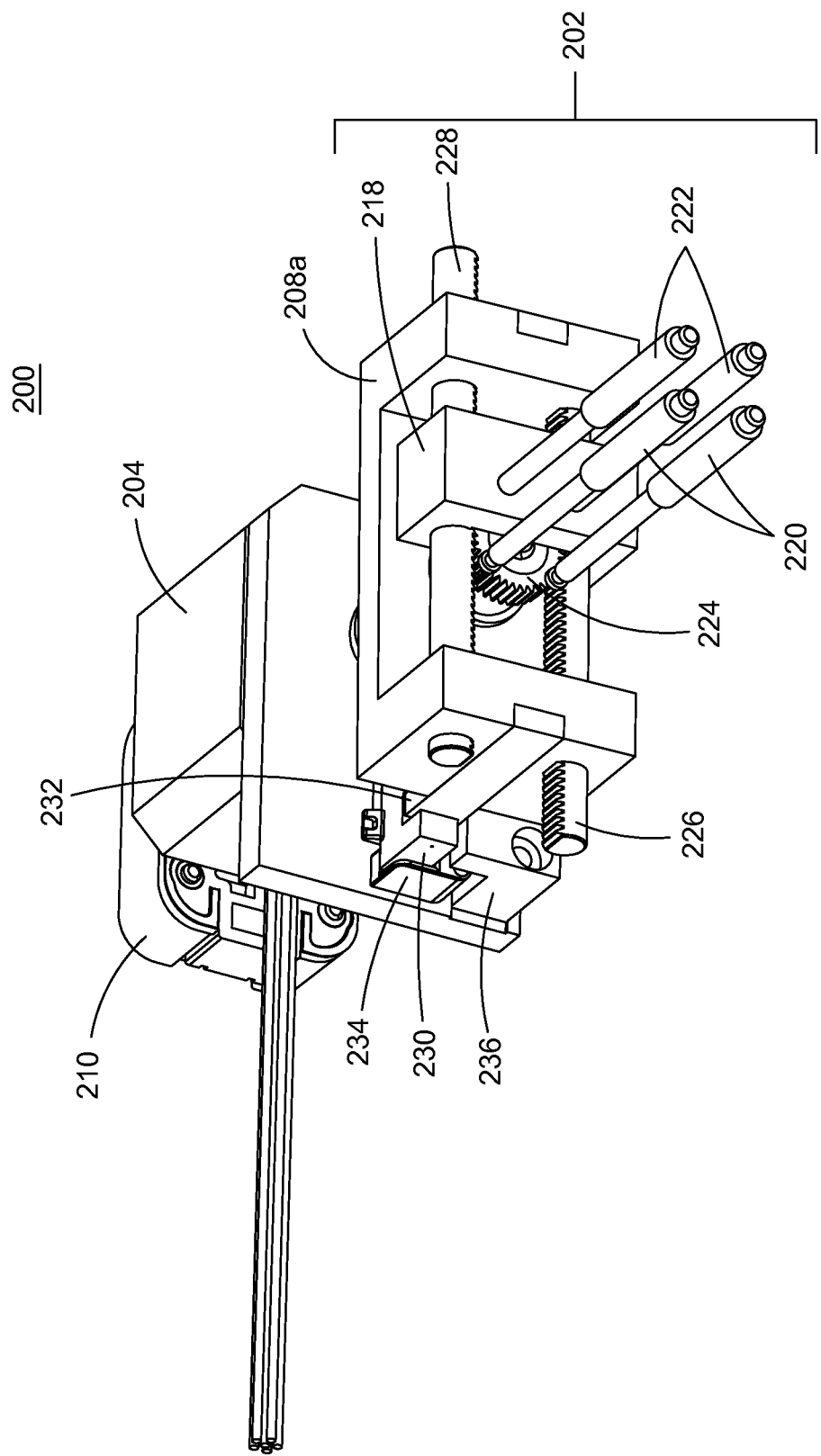
FIG. 2C is a perspective view of the pick and place device shown in FIG. 2A with a finger mount removed and illustrating additional components.
Figure 2D:
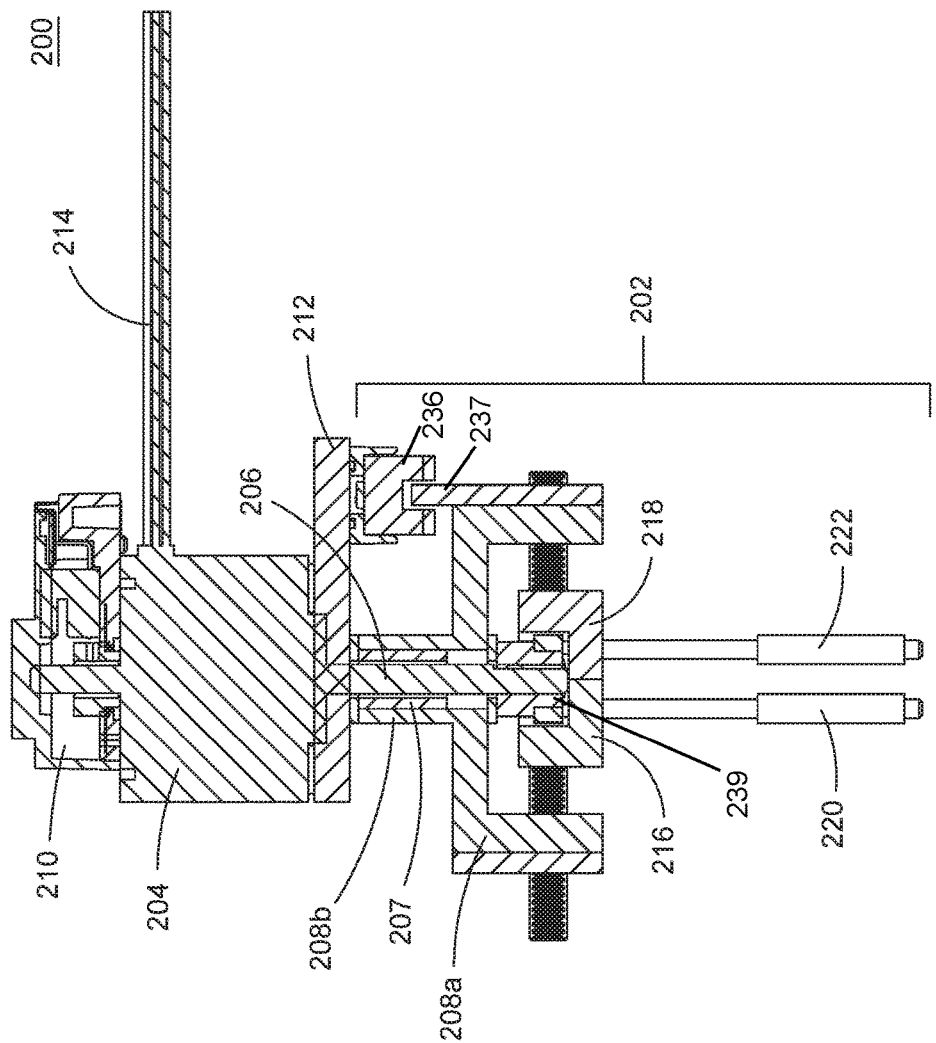
FIG. 2D is a cross sectional view of the exemplary pick and place device shown in FIG. 2A.

FIG. 2A is a perspective view of an exemplary pick and place device 200, according to an embodiment. FIG. 2B is a perspective view of the pick and place device 200 shown in FIG. 2A illustrating components of the gripper assembly 202. FIG. 2C is a perspective view of the pick and place device 200 with the first movable finger mount 216 removed from FIG. 2C to illustrate additional components. FIG. 2D is a cross sectional view of the exemplary pick and place device 200 shown in FIG. 2A.

Referring generally to FIG. 2A through FIG. 2D, the pick and place device 200 includes a gripping assembly 202. The gripping assembly 202 includes yoke 208, movable finger mounts 216 and 218 and fingers 220 and 222. Pick and place device 200 also includes a single motor 204 and a motor shaft 206 coupled to the single motor 204 and configured to rotate. The yoke 208 includes a lower portion 208(a) and an upper portion 208(b).

The yoke 208 is selectively coupled to the rotatable motor shaft 206. In the embodiments described herein, when the yoke 208 is rotating with the rotatable motor shaft 206, the yoke 208 is coupled to the rotatable motor shaft 206. When the yoke 208 is not rotating with the rotatable motor shaft 206, the yoke 208 is uncoupled from the rotatable motor shaft 206. For example, the yoke 208 may be stopped from rotating and be uncoupled from the rotatable motor shaft 206 by stopper 236 or other components (e.g., one-way motion device or sprag clutch) as described in more detail below.

The pick and place device 200 may also include an encoder 210 (e.g., an optical encoder) configured to generate a number of pulses per revolution of the motor 204. For example, the encoder 210 may be configured to generate a number of pulses per revolution of the yoke 208 when it is moving with the motor shaft 206.

The pick and place device 200 may also include a mounting bracket 212. In some embodiments, pick and place device 200 may also include power cord 214. Embodiments may also include pick and place devices having other power sources (e.g., batteries).

As shown in FIG. 2B, gripping assembly 202 may include a first movable finger mount 216 and a second movable finger mount 218 each coupled to the rotatable motor shaft 206. Gripping assembly 202 may also include a first movable rack gear 226 and a second movable rack gear 228. One of the movable rack gears (e.g., gear 228) is fixedly attached to one movable finger mount (e.g., finger mount 216) and the other movable rack gear (e.g., gear 226) is fixedly attached to the other movable finger mount (e.g., finger mount 218). The first movable rack gear 226 and the second movable rack gear 228 are configured to move in a linear direction (231 shown in FIG. 3A through FIG. 3C) relative to the yoke 208 within apertures in the yoke 208 in response to the rotation of the motor shaft 206 when the yoke 208 is uncoupled from the rotatable motor shaft 206.

Gripping assembly 202 may also include a first set of fingers 220 extending substantially perpendicular from a bottom of the first movable finger mount 216. The first set of fingers 220 are configured to move in the linear direction (231 shown in FIG. 3A through FIG. 3C) with the first movable finger mount 216 when the yoke 208 is uncoupled from the rotatable motor shaft 206 and rotate with the yoke 208 when the yoke 208 is coupled to the rotatable motor shaft 206. Gripping assembly 202 may also include a second set of fingers 222 extending substantially perpendicular from a bottom of the second movable finger mount 218. The second set of fingers 222 are also configured to move in the linear direction (231 shown in FIG. 3A through FIG. 3C) with the second movable finger mount 218 when the yoke 208 is uncoupled from the rotatable motor shaft 206 and rotate with the yoke 208 when the yoke 208 is coupled to the rotatable motor shaft 206.

Embodiments may include any number of fingers configured to grip an item to be transported between locations of an analyzer. The number, shape of the fingers and spacing between each finger may depend on different factors, including the shape, size and weight of the items to be carried and the ability to read information (e.g., bar codes) on the items that are gripped and rotated by the pick and place device.

In some embodiments, a distal end of one or more fingers may be configured to increase friction between the fingers and items to be gripped transported between locations of an analyzer. For example, a distal end of one or more fingers may include a high friction material, such as rubber. In some embodiments, the distal end of the fingers may include a knurling surface cut or rolled into the surface of the fingers to provide the fingers with a better grip on items. Examples of knurling surfaces may include a knurled criss-cross pattern, a pattern of a series of straight ridges or a helix of straight ridges.

As shown in FIG. 2C, the pick and place device 200 may also include a pinion gear 224 (hereinafter pinion). Pinion 224 may be coupled to the rotatable motor shaft 206 (shown in FIG. 2D) and configured to rotate with the rotatable motor shaft 206. The first movable rack gear 226 and the second movable rack gear 228 each include a plurality of teeth. Pinion 224 also includes a plurality of teeth. The first movable rack gear 226 and the second movable rack gear 228 are each movably coupled to the pinion 224 via the teeth disposed on the rack gears 226 and 228 and the teeth disposed on the pinion 224. In this manner, the rotational motion of the pinion 224 (rotating with the motor shaft 206) may be converted to linear motion of the movable rack gears 226 and 228.

The pick and place device 200 may also include a home sensor 230 configured to emit a beam and a home flag 232 disposed on or coupled to the yoke 208 and configured to block the beam of the home sensor 230 and provide a home position of the gripping assembly 202 (e.g., home position of the yoke 208). In some embodiments, the pick and place device 200 may include a home sensor holder 234 configured to hold the home sensor 230. In some embodiments, a position of the yoke 208 along its rotation may be determined by a number of pulses generated as the yoke 208 moves from the home position. Because of the width (e.g., ¼ inch) of the home flag, however, the yoke 208 may move along its rotation and a number of pulses may be generated while the beam of light is still blocked by the home flag 232. Accordingly, during this movement of the yoke 208, the position of the yoke 208 along its rotation may not be determined.

As shown in FIG. 2B, the pick and place device 200 may also include a pair of springs 227. The springs 227 are not shown in the other figures to show other components and for explanation purposes. As shown in FIG. 2B, each spring 227 is fixedly coupled between the yoke 208 and one of the finger mounts 216 and 218. Each spring 227 is configured to apply an inward force to one movable finger mount toward the other movable finger mount in the linear direction 231 for gripping items (not shown). In the event of a power loss, each of the springs 227 may also be configured to continue to apply the inward force to the first movable finger mount 216 and the second movable finger mount 218, thereby maintaining the fingers 220 and 222 in a gripping position and preventing items from being released from the pick and place device 200. The springs 227 may provide the pick and place device 200 with a gripping force without the use of external power sources, such as hoses or wires. The number, location and size of springs 227 shown in FIG. 2B is merely exemplary. Embodiments may include any number of springs having locations and sizes different from the spring 227 shown in FIG. 2B.

As shown in FIG. 2D, the pick and place device 200 may include bearing (e.g., bushing) 207. The bearing 207 is disposed between the motor shaft 206 and the upper portion 208(b) of yoke 208 to center the yoke 208 on the motor shaft 206. The bearing 207 also prevents wear and tear on the motor shaft 206 and the yoke 208 by providing lower friction.

The pick and place device 200 may be used to perform pick and place operations for transfer of the items between different locations, such as between one location of the analyzer to another location of the analyzer for subsequent processing. That is, pick and place device 200 may grip (pick) items from one location and release (place) the items at another location. The gripping motion and release motion of pick and place device 200 is now described with reference to FIG. 3A to FIG. 3C.

Figure 3A:
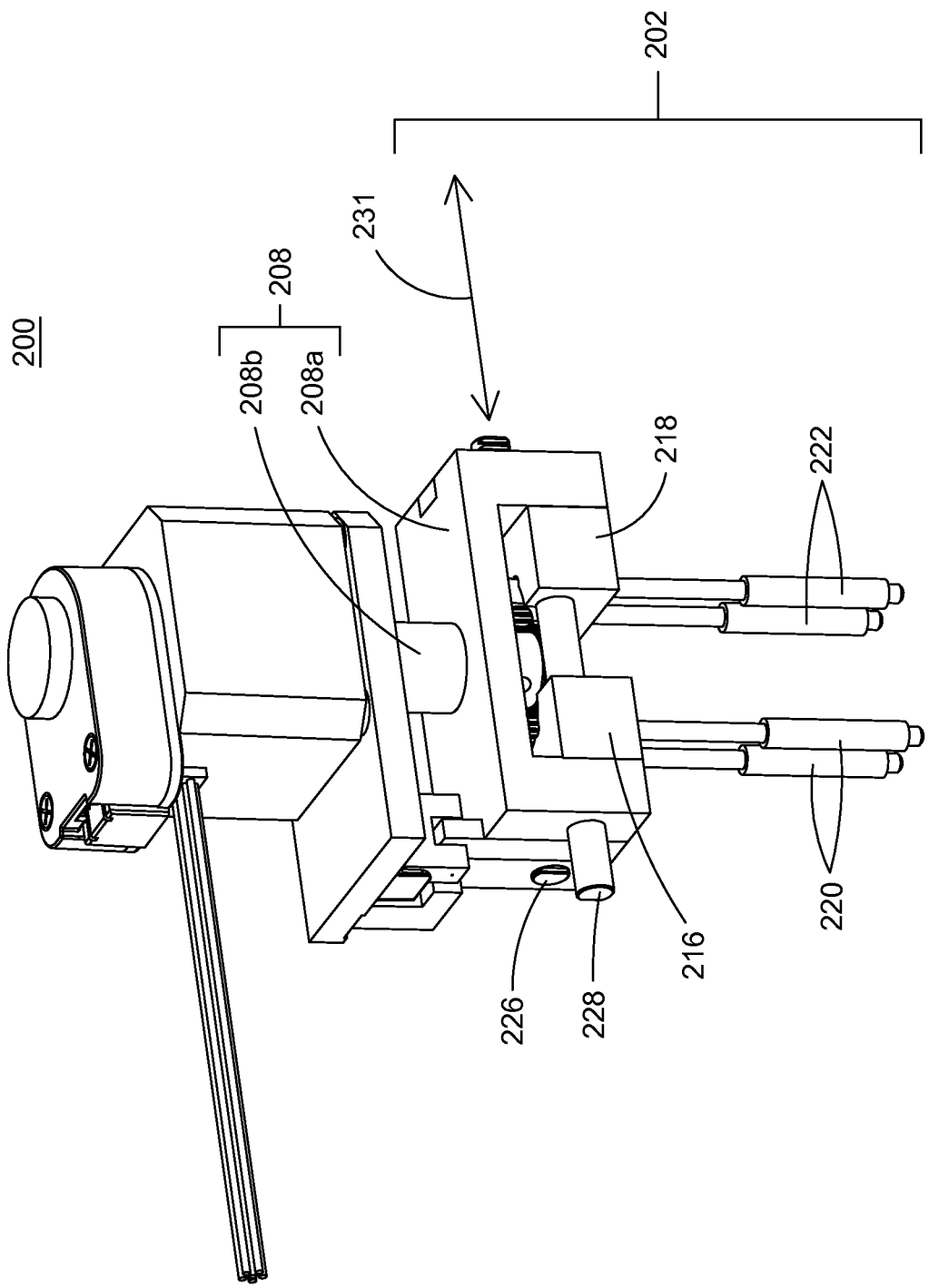
FIG. 3A is a perspective view of the pick and place device with the gripping assembly in an open position.
Figure 3B:
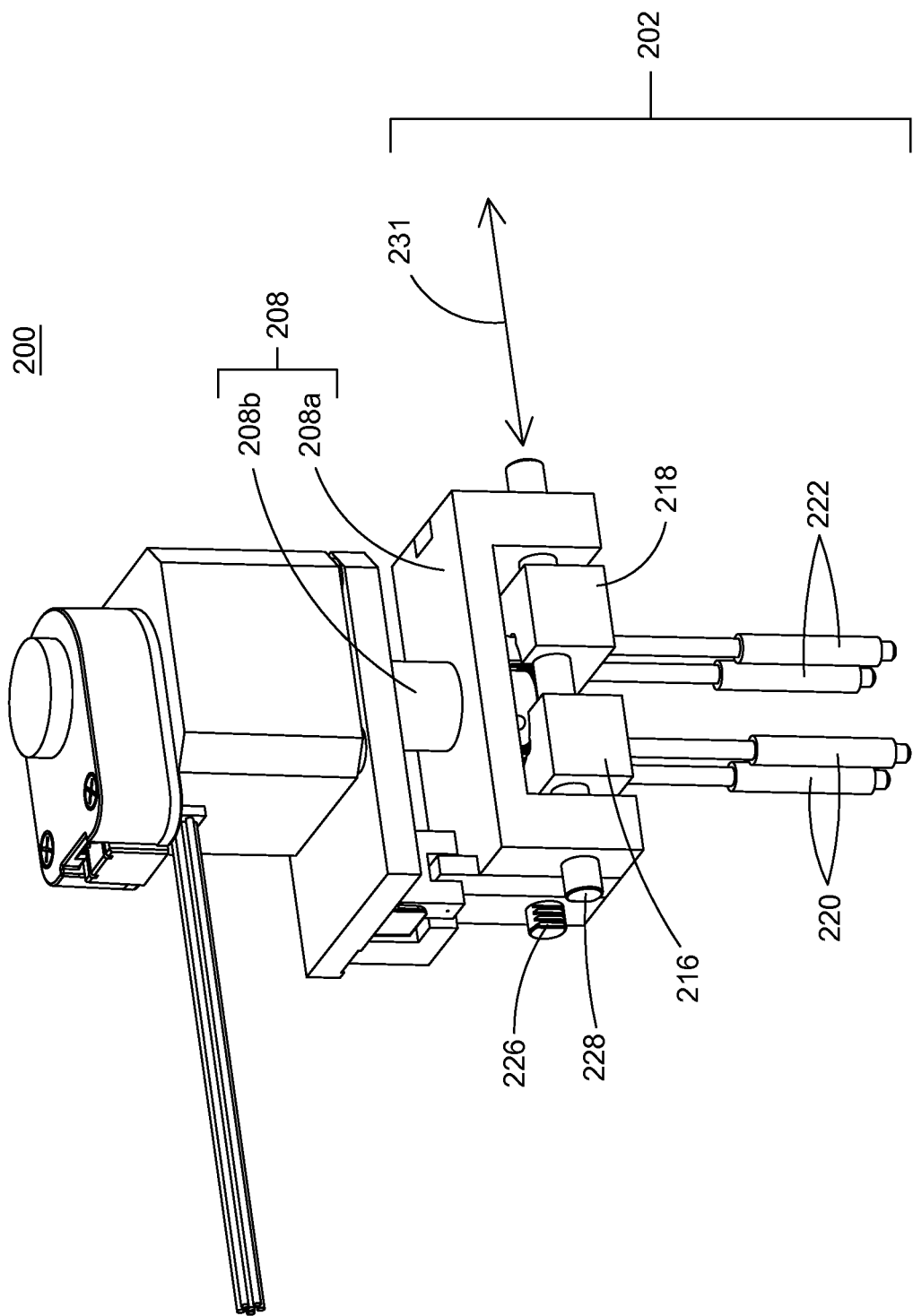
FIG. 3B is a perspective view of the pick and place device with the gripping assembly in a partially extended position.
Figure 3C:
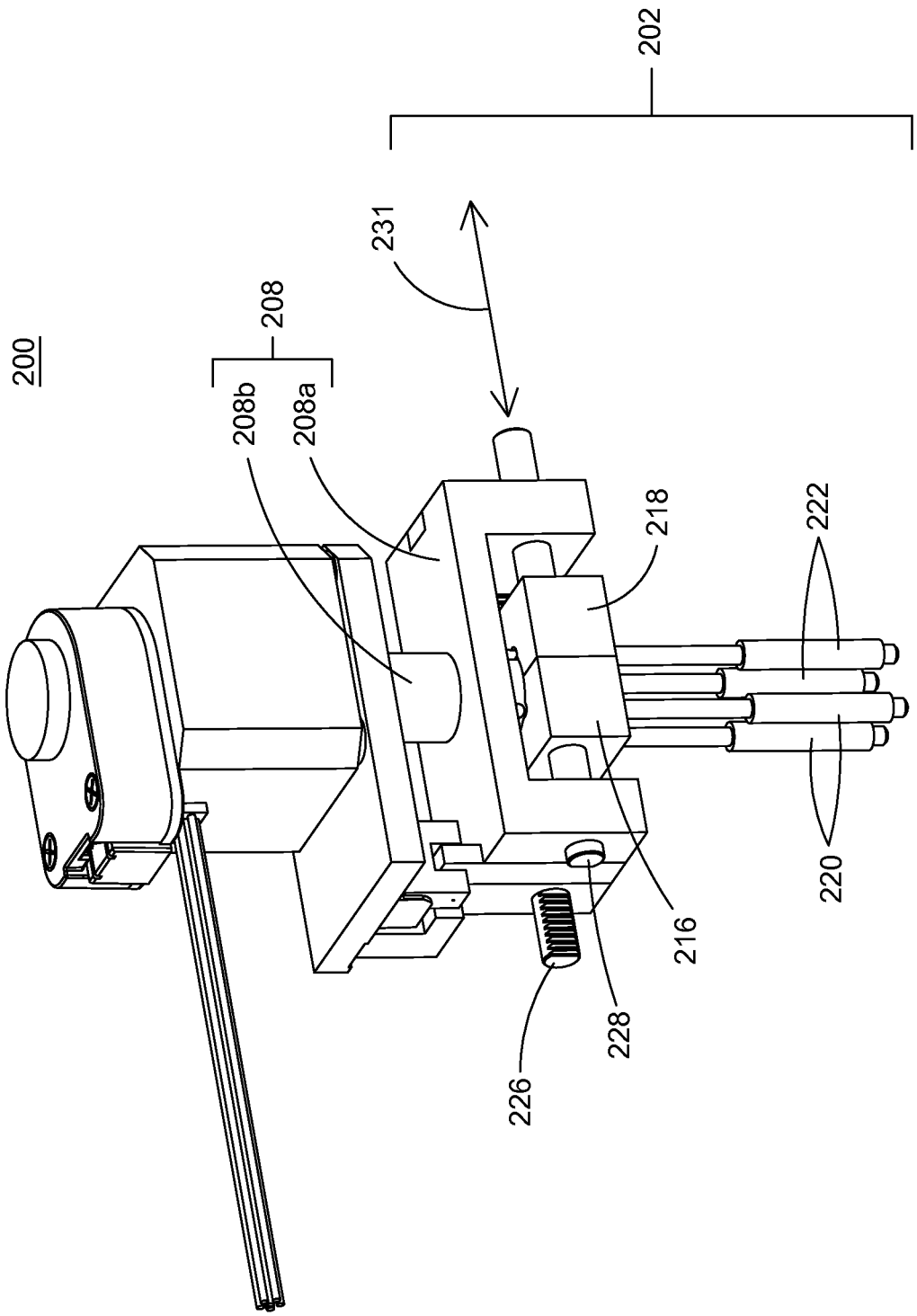
FIG. 3C is a perspective view of the pick and place device with the gripping assembly in a closed position.
Figure 4A:
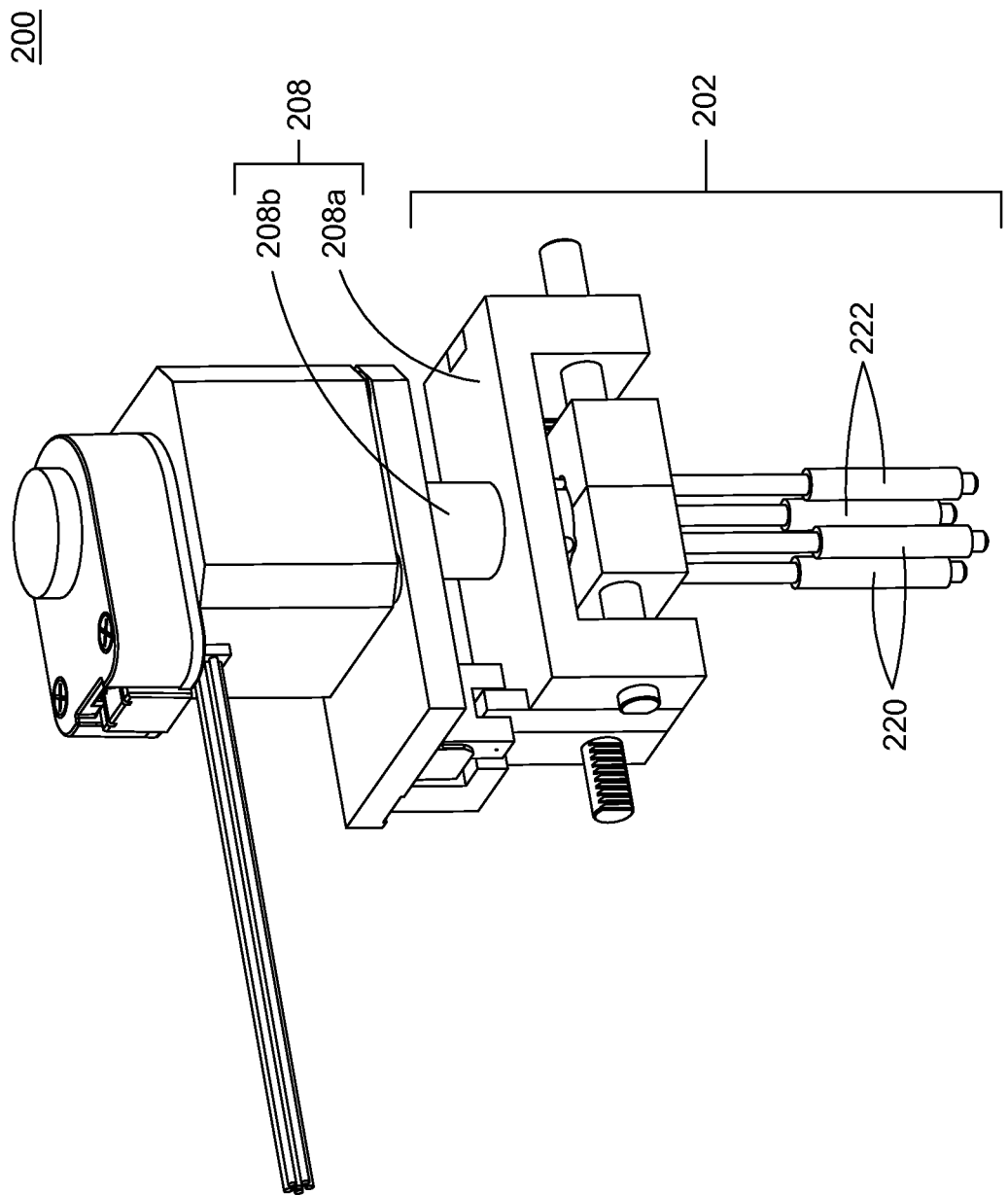
Figure 4D:
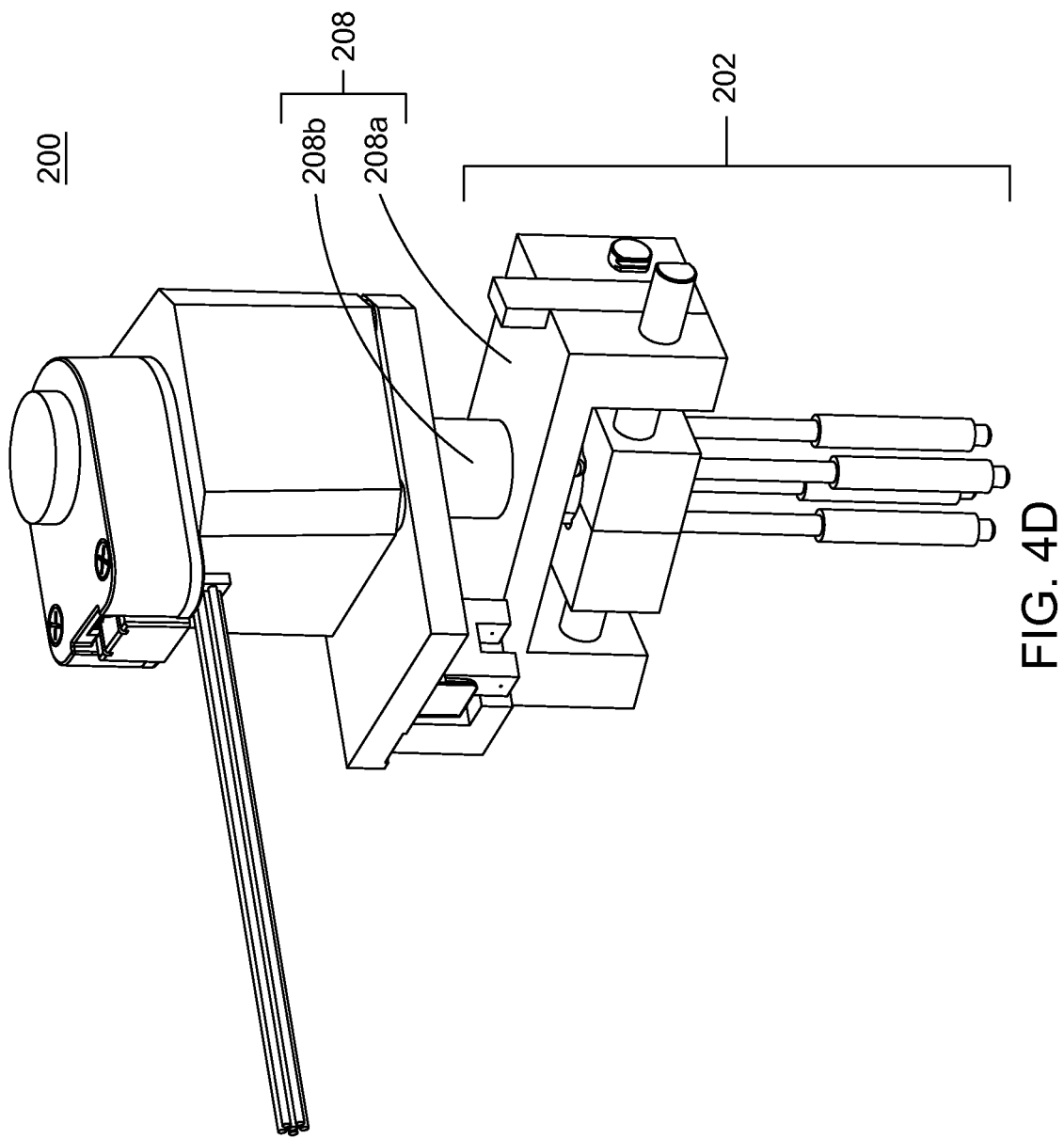
Figure 4F:
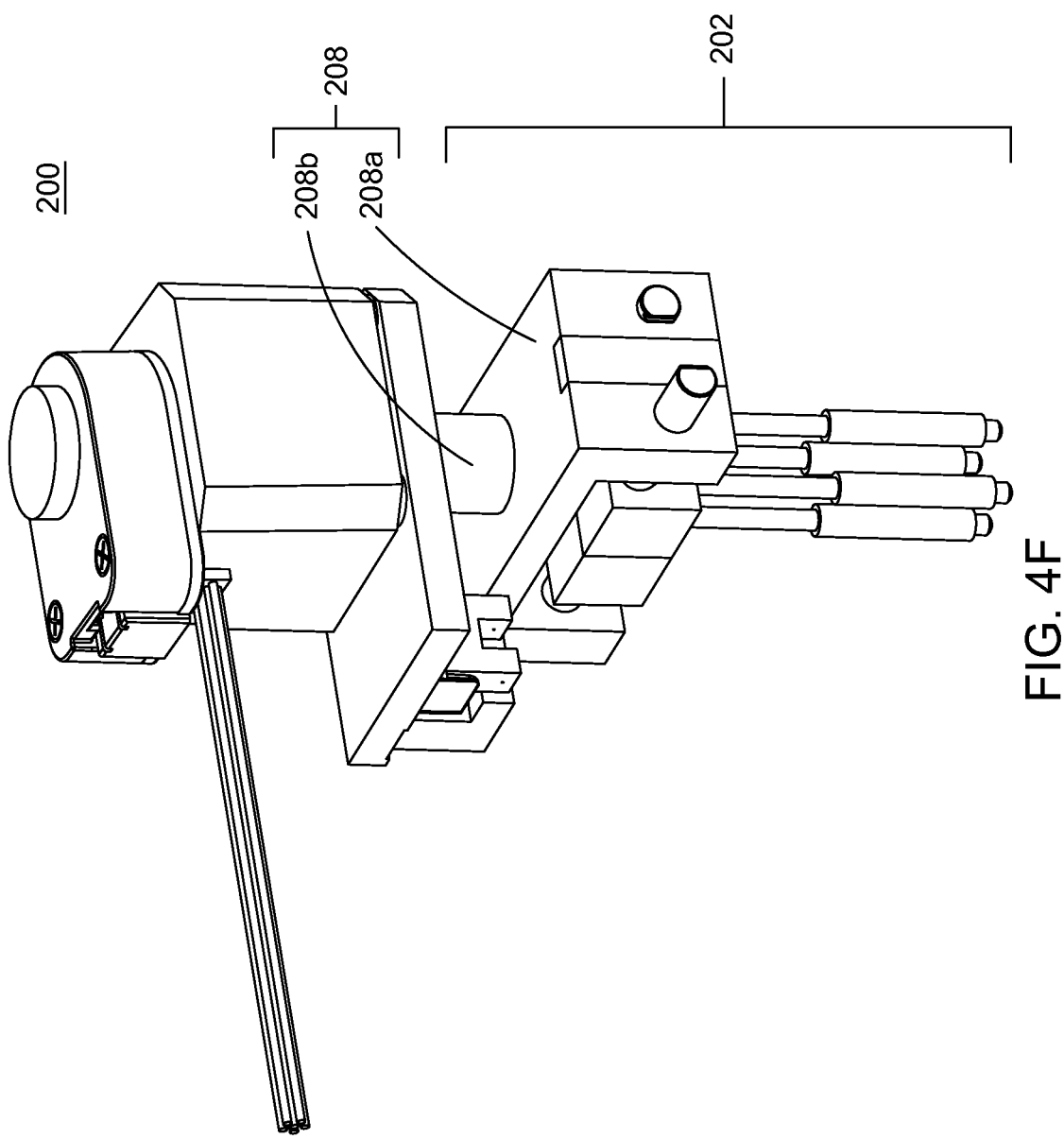
Figure 4G:
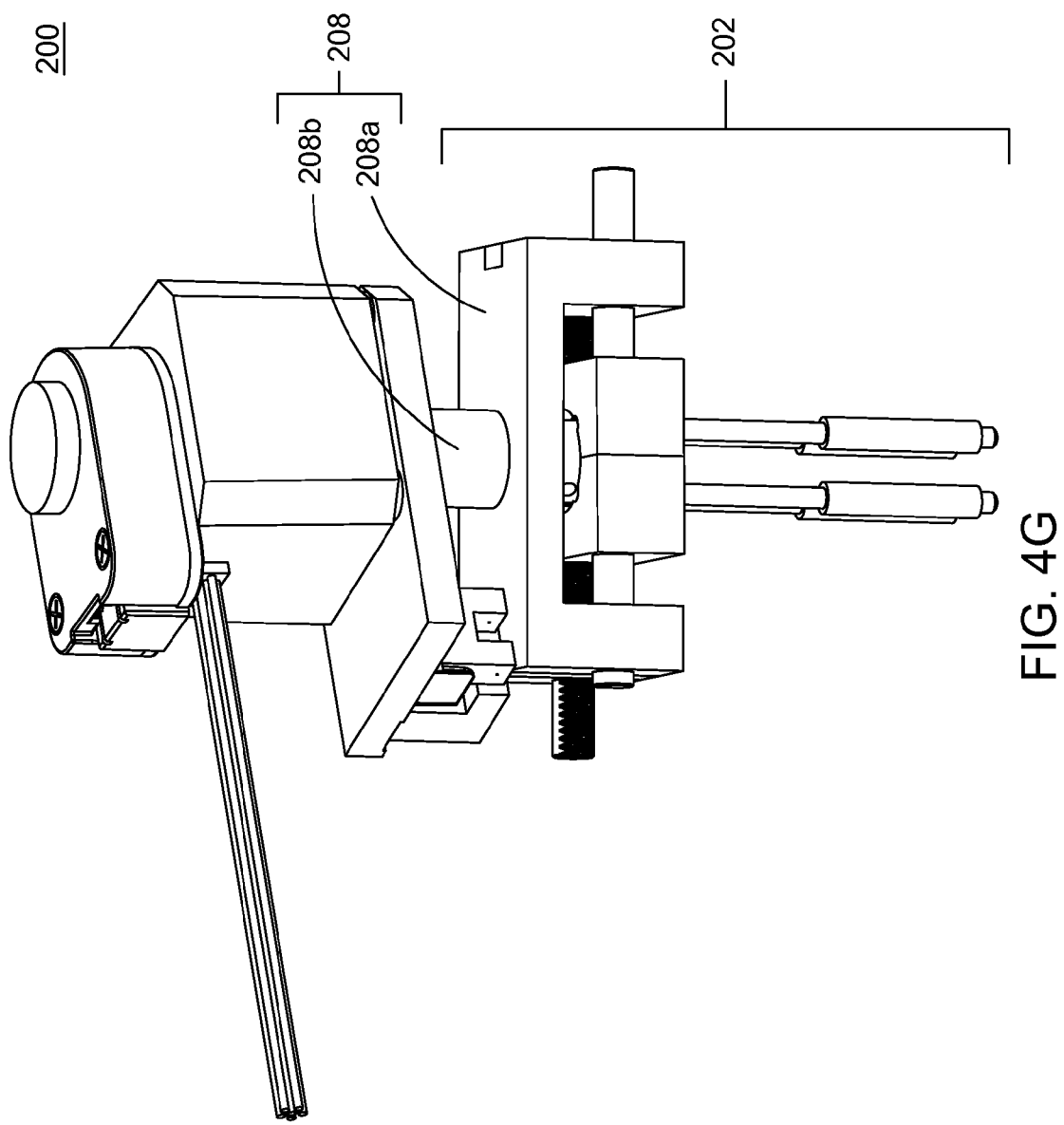
Figure 4I:
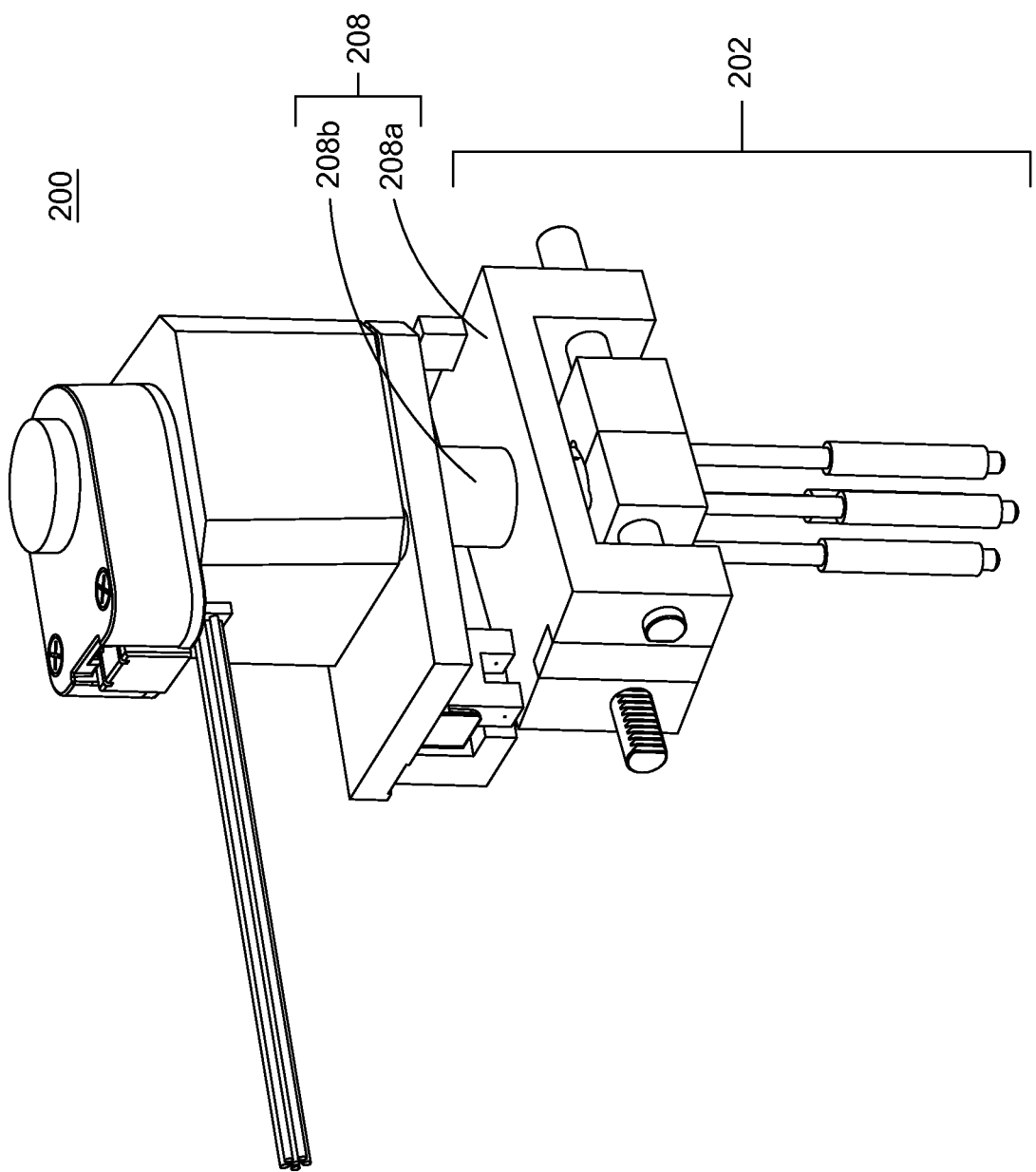
Figure 4J:
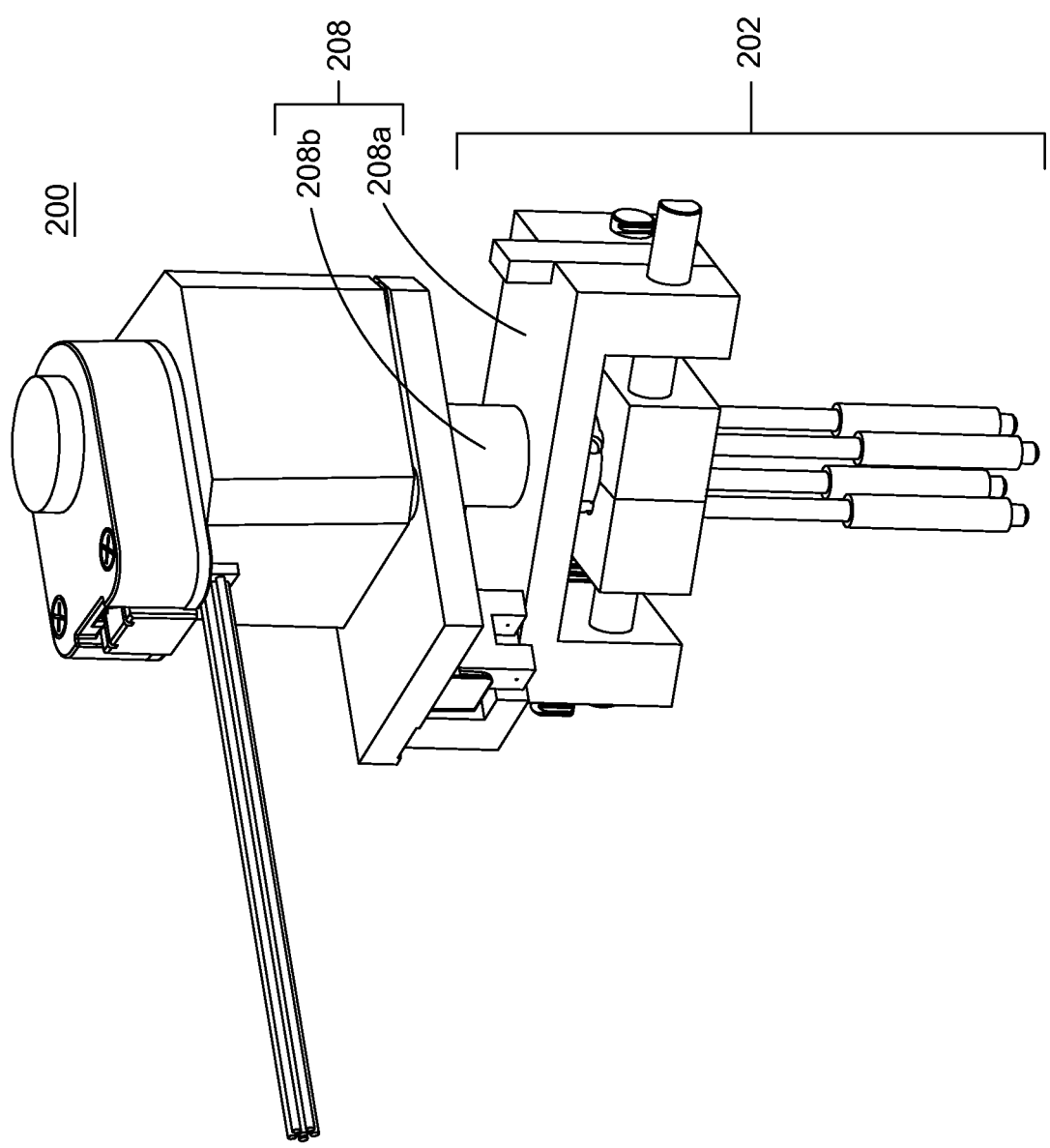
Figure 4K:
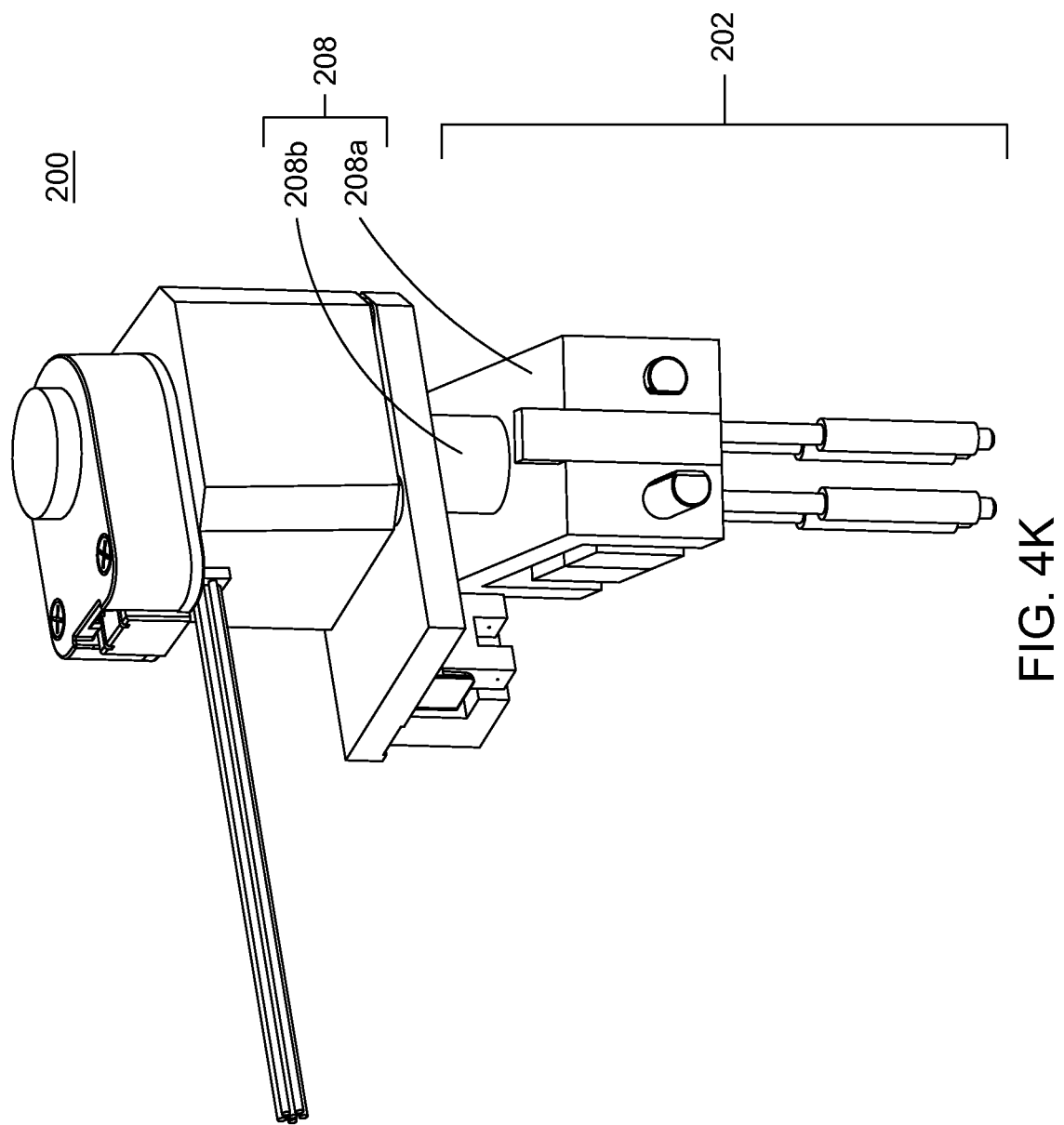
Figure 4L:
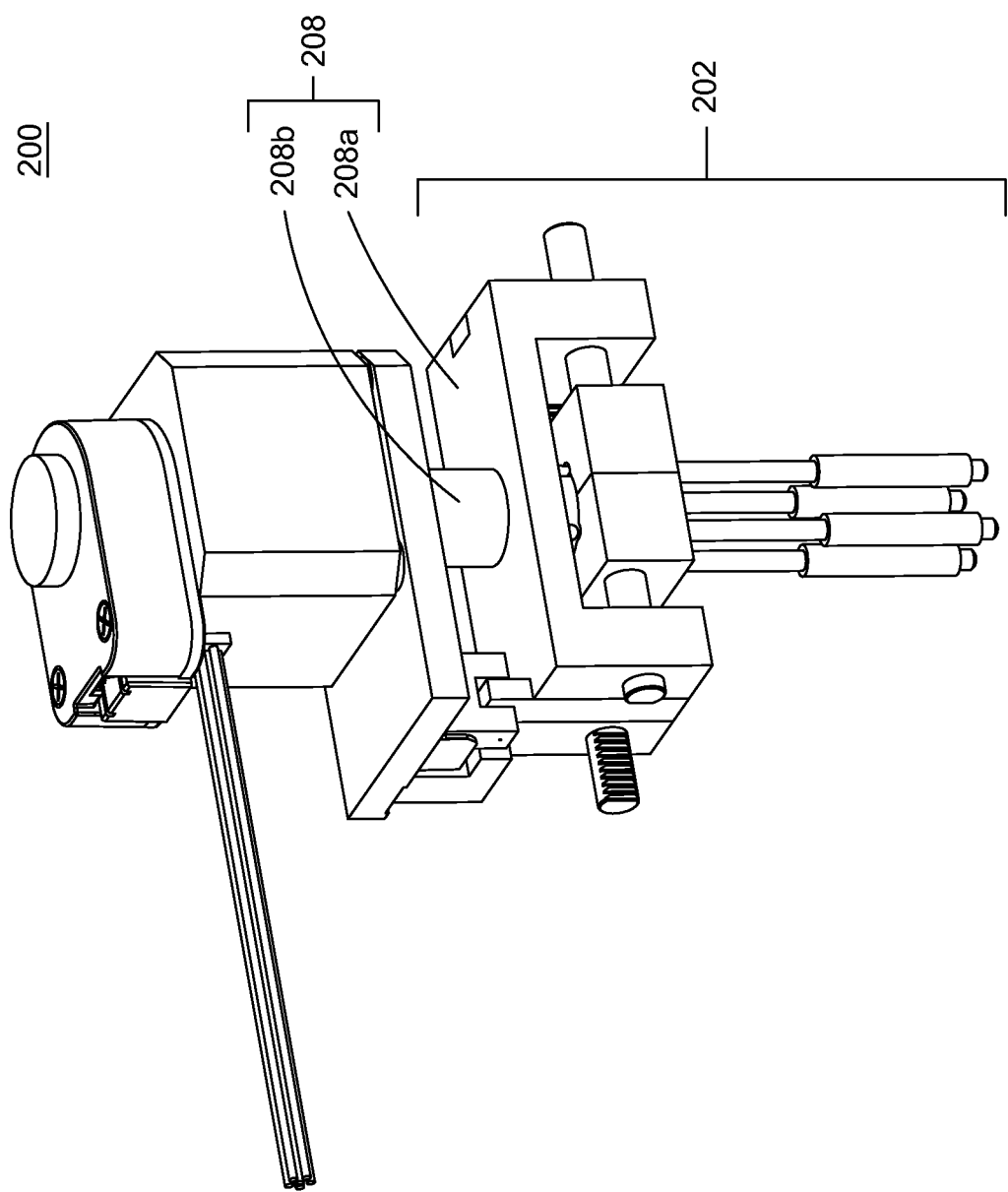

FIG. 3A is a perspective view of the pick and place device 200 with the gripping assembly 202 in an open position. FIG. 3B is a perspective view of the pick and place device 200 with the gripping assembly 202 in a partially extended position. FIG. 3C is a perspective view of the pick and place device 200 with the gripping assembly 202 in a closed position.

When the yoke 208 stops rotating (e.g., via stopper 236), the yoke 208 becomes uncoupled from the rotatable motor shaft 206 and the motor shaft 206 is also free to rotate clockwise and counterclockwise. In this manner, the motor shaft 206, connected to pinion gear 224 (shown in FIG. 2C), causes pinion gear 224 to rotate and the finger mounts 216 and 218 to move linearly toward each other or away from each other depending on the rotational direction of the motor shaft 206 and the pinion gear 224.

Referring generally to FIG. 3A to FIG. 3C, when the yoke 208 is uncoupled from the rotatable motor shaft 206 (e.g., when the yoke 208 is stopped from rotating by stopper 236 or other components described below), the rotation of the motor shaft 206 in the clockwise or counterclockwise direction causes pinion 224 (shown in FIG. 2C) to rotate in a first direction, thereby causing the first movable rack gear 226 to move in linear direction 231 and second movable rack gear 228 to move opposite the first movable rack gear 226 in the linear direction 231. The movement of the first movable rack gear 226 and the second movable rack gear 228 cause the first movable finger mount 216 and the second movable finger mount 218 to move toward each other in the linear direction 231 from the open position shown in FIG. 3A to the partially extended position shown in FIG. 3B and then to closed position shown in FIG. 3C to grip an item (not shown).

When the first movable finger mount 216 and the second movable finger mount 218 are in the closed position shown in FIG. 3C, the motor shaft 206 may rotate in the other of the clockwise or counterclockwise direction, causing the pinion 224 (shown in FIG. 2C) to rotate in a second direction opposite the first direction. The torque of the motor shaft increases and overcomes the inward forces applied by the springs 227, causing the first movable rack gear 226 and second movable rack gear 228 to move away from each other in the linear direction 231 and the first set of fingers 220 to move away from the second set of fingers 222. Accordingly, the gripping assembly 202 may move from the closed position shown in FIG. 3C to the partially extended position shown in FIG. 3B and then to the open position shown in FIG. 3A to release items.

In the embodiment shown in FIG. 3A to FIG. 3C, movable rack gear 228 is connected to movable finger mount 216 such that the movement of movable rack gear 228 in the linear direction 231 causes movable finger mount 216 to move in the linear direction 231. Further, movable rack gear 226 is connected to movable finger mount 218 such that the movement of movable rack gear 226 in the linear direction 231 causes movable finger mount 218 to move in the linear direction 231. In another embodiment, movable rack gear 228 may be connected to movable finger mount 218 and movable rack gear 226 may be connected to movable finger mount 216. For simplified explanation, however, the configuration shown in FIG. 3A to FIG. 3C is used to describe the gripping motion and release motion of pick and place device 200.

The first set of fingers 220 move in the linear direction 231 with the first movable finger mount 216 toward the second set of fingers 222 and the second set of fingers 222 move in the linear direction 231 with the second movable finger mount 218 toward the first set of fingers 220. Accordingly, the gripping assembly 202 may move from the open position shown in FIG. 3A to the partially extended position shown in FIG. 3B and then to the closed position shown in FIG. 3C to grip items at a location.

FIG. 4A through FIG. 4L are perspective views of the pick and place device 200 at different states of the gripping assembly's 202 rotational motion, according to an embodiment. In some embodiments, the rotation of gripping assembly 202 may be used to reorient items during operation in a clinical diagnostics automation system. For example, an item may be gripped by fingers via the linear motion of the fingers described in FIG. 3A to FIG. 3C when the yoke 208 is uncoupled from the rotatable motor shaft 206 and the item, while gripped by the fingers, may be rotated when the yoke 208 is coupled to the rotatable motor shaft 206 to present an item indicator (e.g., bar code label) on the item to an item identifier (e.g., scanner) to determine or confirm identification of the item and facilitate performance of ordered tests and reporting results of the tests.

As the motor shaft 206 rotates, the yoke 208 is coupled to the rotatable motor shaft 206 and rotates (e.g., in a clockwise direction or a counter-clockwise direction) with the motor shaft 206. FIG. 4A through FIG. 4G illustrate the rotational motion of the yoke 208 in a first rotational direction (e.g., counter-clockwise direction indicated by arrow 402 in FIG. 4B) and FIG. 4H through FIG. 4L illustrate rotational motion of the yoke 208 in an opposite second rotational direction (e.g., clockwise direction indicated by arrow 404 in FIG. 4H). For example, the yoke 208 may rotate from its position shown in FIG. 4A to its position shown in FIG. 4B in the counter-clockwise direction indicated by arrow 402 shown in FIG. 4B. The yoke 208 may continue to rotate in the counter-clockwise direction through its positions shown in FIG. 4C to FIG. 4G. The yoke 208 may also rotate from its position shown in FIG. 4G to its position shown in FIG. 4H in the clockwise direction indicated by arrow 404 shown in FIG. 4H. The yoke 208 may continue to rotate in the counter-clockwise direction through its positions shown in FIG. 4I to FIG. 4L. The rotation of the yoke 208 is not limited by the positions of the yoke shown in FIG. 4A to FIG. 4L. Further, embodiments may include stopping the rotation of the yoke 208 at any position and starting the rotation of the yoke 208 in either rotational direction from any position.

In some embodiments, the yoke 208 may be configured to rotate with the motor shaft 206 in the first rotational direction (e.g., the clockwise direction or the counter-clockwise direction) and the second rotational direction (e.g., other of the clockwise direction and the counter-clockwise direction). For example, the pick and place device 200 may include a stopper 236 (as shown in FIG. 2B and FIG. 2C). In this embodiment, when the yoke 208 is rotating in the first rotational direction (yoke 208 is coupled to the rotatable motor shaft 206) and the stopper 236 contacts a portion extending from the gripper assembly 202, the yoke 208 is prevented from further rotating in the first direction and the yoke 208 becomes uncoupled from the rotatable motor shaft 206. Also, when the yoke 208 is rotating in the second direction and the stopper 236 contacts the portion extending from the gripper assembly 202, the yoke 208 is prevented from further rotating in the second direction.

In another embodiment, the pick and place device 200 may include a spring loaded stopper (not shown). In this embodiment, the yoke 208 is also configured to rotate with the motor shaft 206 in the first direction and the second direction when the yoke 208 is coupled to the rotatable motor shaft 206. But the yoke 208 is prevented from further rotating in one of the first rotational direction or the second rotational direction when the spring loaded stopper 236 contacts a protruding portion 237 (FIG. 2D) extending from the gripper assembly 202. When the yoke 208 is prevented from rotating, via the one-way motion device in the other of the first rotational direction or the second rotational direction, the yoke 208 is uncoupled from the rotatable motor shaft 206. The yoke 208 is free, however, to further rotate continuously in the other of the first rotational direction or the second rotational direction.

In some embodiments, the yoke 208 may be selectively coupled to the motor shaft 206 via elements that permit rotation of the motor shaft 206 without rotation of the yoke 208. For example, in one embodiment, the yoke 208 may be configured to rotate in one of the first rotational direction or the second rotational direction but prevented from rotating in the other of the first rotational direction or the second rotational direction. Exemplary pick and place device 200 may include a one-way motion device 239 (FIG. 2D), (e.g., one-way clutch or sprag clutch) configured to prevent the yoke 208 from rotating in one of the first rotational direction or the second rotational direction. When the yoke 208 is coupled to the rotatable motor shaft 206, the yoke 208 is configured to rotate with the rotatable motor shaft 206 in one of the first rotational direction or the second rotational direction. When the yoke 208 is prevented from rotating, via the one-way motion device in the other of the first rotational direction or the second rotational direction, the yoke 208 is uncoupled from the rotatable motor shaft 206. For example, a one-way clutch may be a hydraulically operated clutch that uses a transmission fluid that is pumped when pressure is exerted by an oil pump to control the clutches and the gear sets. The clutch may include a combination of many gears. A sprag clutch may include non-revolving asymmetric figure-eight shaped sprags. When the motor shaft 206, and hence the clutch rotates in one direction, the rollers slip or free-wheel. When a torque is applied in the opposite direction, however, the rollers tilt slightly, producing a wedging action and binding because of friction. The sprags are spring-loaded so that they lock with very little backlash. In another example, a one-way clutch may use spring-loaded balls on inclined ramps.

In some embodiments, (e.g., spring loaded stopper and one way clutch), the movement of the gripper assembly 202 may proceed as follows. The motor shaft 206 may rotate in a first direction and the yoke 208 may rotate with the motor shaft 206 in the first direction (e.g., clockwise direction or counter-clockwise direction). The motor shaft 206 may stop rotating and the yoke 208 may stop at the home position. The motor shaft 206 may then rotate in a second direction (e.g., the other of the clockwise direction or counter-clockwise direction) opposite the first direction and the movable finger mounts 216 and 218 may then move away from each other (opening fingers) and the springs compress. The yoke 208 does not rotate in the second direction, however, because as described above, further movement in the second direction is prevented (e.g., spring loaded stopper 236) or any movement in the second direction is prevented (e.g., one-way clutch 239). The motor shaft 206 may then be rotated again in the first direction. The movable finger mounts 216 and 218 then begin to move toward each other (closing fingers for gripping an item, such as a sample tube), but the yoke 208 does not rotate until the springs reach equilibrium and a force preventing rotation is no longer applied. The movable finger mounts 216 and 218 continue to move toward each other until the fingers 220 and 222 contact an item.

In some embodiments, the pick and place may be configured to measure the diameter of an item, such as a sample tube. The encoder 210, which may be coupled to the motor shaft 206, and the home sensor 230 may be used to determine how much the first and second movable finger mounts 216 and 218 have opened. For example, the encoder 210 may generate a number of pulses per revolution as the encoder 210 is moving with the rotatable motor shaft 206. The encoder 210 may be reset to a 0 count when the finger mounts 216 and 218 are at rest in a closed position (e.g., fully closed position). The encoder 210 may then generate a number of pulses (e.g., 100 pulses) while the finger mounts 216 and 218 are opening in a linear direction from the fully closed position to the open position (e.g., fully opened position). When the finger mounts 216 and 218 reach the open position, the finger mounts 216 and 218 may then start to move toward each other in the linear direction during which the number of pulses generated by the encoder 210 are counted down (e.g., subtracted) from 100 until the finger mounts 216 and 218 stop moving. The number of pulses subtracted from 100 may determine the size of the tube, and hence the diameter of the tube. For example, if the number of pulses subtracted from 100 is also 100 pulses (back to a net 0 count) or about 100 pulses, it may be determined that the finger mounts 216 and 218 have returned back to the fully closed position or about the fully closed position and that no tube is present in the pick and place device 200. If the number of pulses subtracted from 100 is, for example 80 (resulting in a net 20 count), a small tube may be identified in the pick and place device 200. If the number of pulses subtracted from 100 is, for example 40 (resulting in a net 60 count), a large tube may be identified. Embodiments may include pre-determining sizes of tubes corresponding to a number of net pulses generated by an encoder so that the sizes of tubes may be automatically determined from the number of net pulses generated during use in an in vitro diagnostics automation system. Embodiments may include determining any number of different sized tubes.

In some embodiments, one or more pick and place devices 200 may be part of a clinical diagnostics automation system that may include one or more processors configured to cause movement of the pick and place device 200 and/or movement of components of the pick and place device 200. For example, one or more processors may be configured to cause gripping assembly 202 to switch between: (i) a first state such that the motor 204 cause one or more sets of fingers to move in a linear direction toward and away from one or more second set of fingers of the plurality of fingers; and (ii) a second state such that the motor causes a gripping assembly base (e.g., a yoke) and the plurality of fingers to rotate in a clockwise direction and a counter-clockwise direction. The processor may communicate with one or more other processors (e.g., local processor or central processor) in an in vitro diagnostics automation system. In the embodiments described herein, the rotation motion may be either in a first direction (e.g., clockwise direction or a counter-clockwise direction) and a second direction (e.g., the other of the clockwise direction or a counter-clockwise direction) opposite the first direction. Further, whether the direction of rotation is clockwise or counter-clockwise depends upon a perspective of viewing (e.g., looking down or looking up) with respect to the gripping assembly 202.

Figure 5:
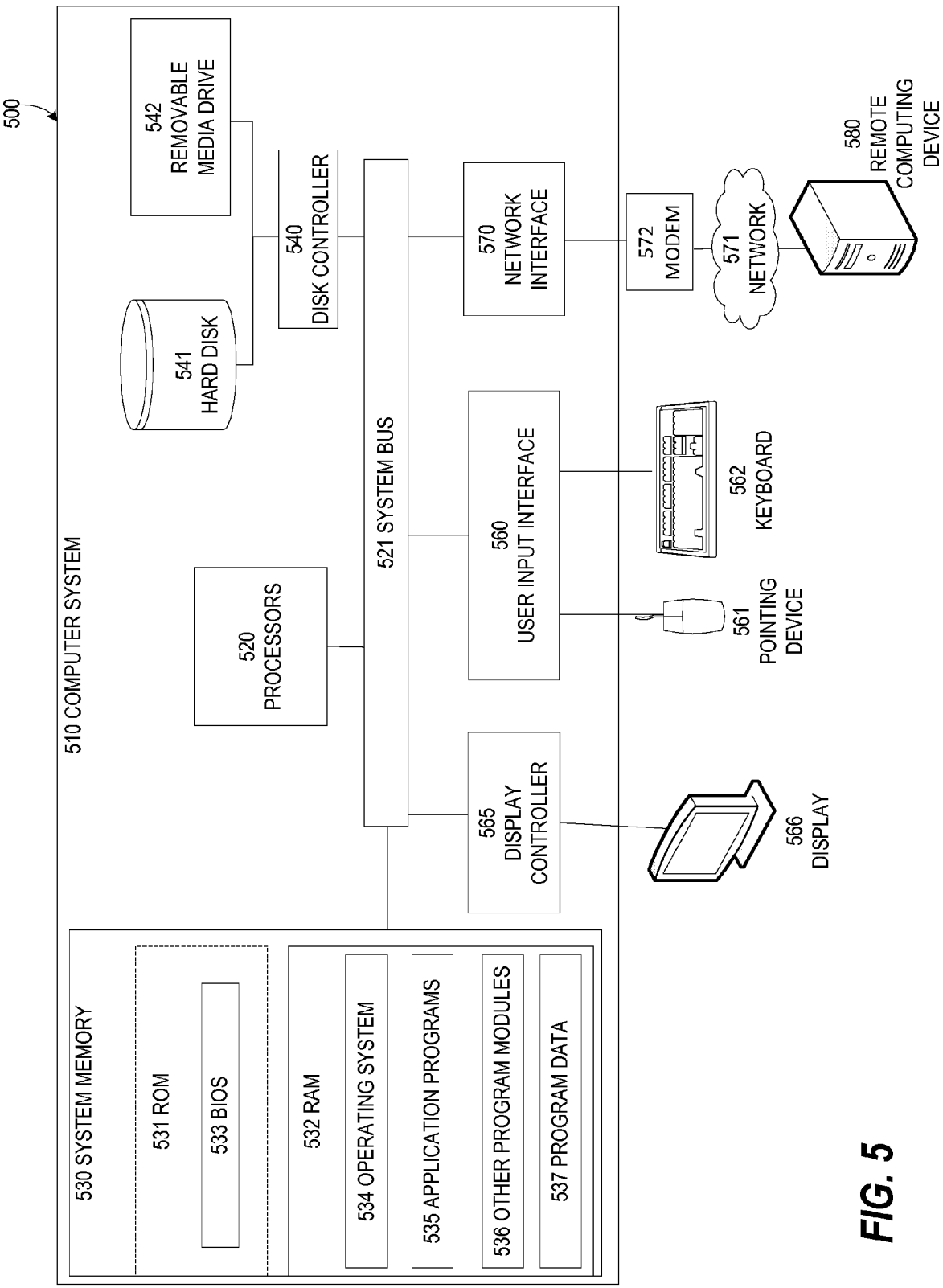
FIG. 5 illustrates an example of a computing environment within which embodiments of the invention may be implemented.

FIG. 5 illustrates an example of a computing environment within which embodiments of the invention may be implemented. Computing environment 500 may include computer system 510, which is one example of a computing system upon which embodiments of the invention may be implemented. As shown in FIG. 5, the computer system 510 may include a communication mechanism such as a bus 521 or other communication mechanism for communicating information within the computer system 510. The system 510 further includes one or more processors 520 coupled with the bus 521 for processing the information. The processors 520 may include one or more CPUs, GPUs, or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a magnetic hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display or monitor 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any non-transitory, tangible medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer 510. When used in a networking environment, computer 510 may include modem 572 for establishing communications over a network 571, such as the Internet. Modem 572 may be connected to system bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computing system 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite, or any other wireless connection methodology generally known in the art. Additionally, several networks may work alone or in communication with each other to facilitate communication in the network 571.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The GUI also includes an executable procedure or executable application. The executable procedure or executable application conditions the display processor to generate signals representing the GUI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the GUI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 5. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

I claim:

1. A pick and place device for use in an in vitro diagnostics automation system comprising:
a motor,
a rotatable motor shaft coupled to the motor and configured to rotate; and a gripping assembly comprising:
  a yoke selectively coupled to the rotatable motor shaft and configured to rotate with the rotatable motor shaft when the yoke is coupled to the rotatable motor shaft;
  a first movable finger mount and a second movable finger mount each coupled to the rotatable motor shaft and configured to move toward each other and away from each other in a linear direction responsive to the rotation of the motor shaft when the yoke is uncoupled from the rotatable motor shaft;
  a first set of fingers extending from the first movable finger mount and configured to: (i) move in the linear direction with the first movable finger mount when the yoke is uncoupled from the rotatable motor shaft; and (ii) rotate with the yoke when the yoke is coupled to the rotatable motor shaft;
  a second set of fingers extending from the second movable finger mount and configured to: (i) move in the linear direction with the second movable finger mount when the yoke is uncoupled from the rotatable motor shaft; and (ii) rotate with the yoke when the yoke is coupled to the rotatable motor shaft;
  a first spring fixedly coupled between the yoke and the first movable finger mount, the first spring configured to apply a first inward force to the first movable finger mount toward the second movable finger mount in the linear direction; and
  a second spring fixedly coupled between the yoke and the second movable finger mount, the second spring configured to apply a second inward force to the second movable finger mount toward the first movable finger mount in the linear direction.

2. The pick and place device of claim 1, further comprising:
  a pinion coupled to the rotatable motor shaft and configured to rotate with the rotatable motor shaft;
  a first movable rack gear connected to the first movable finger mount and movably coupled to the pinion and configured to move the first movable finger mount in the linear direction when the pinion rotates; and
  a second movable rack gear connected to the second movable finger mount and movably coupled to the pinion and configured to move the second movable finger mount in the linear direction when the pinion rotates.

3. The pick and place device of claim 1, further comprising:
  an encoder coupled to the rotatable motor shaft and configured to generate a number of pulses per revolution of the motor when the encoder is moving with the rotatable motor shaft;
  a home sensor configured to emit a beam; and
  a home flag disposed on or coupled to the yoke and configured to block the beam of the home sensor and provide a home position of the gripping assembly.

4. The pick and place device of claim 1, wherein the yoke is further configured to rotate in a clockwise direction and a counter-clockwise direction with the rotatable motor shaft.

5. The pick and place device of claim 4, further comprising: a stopper; and
  a protruding portion extending from the gripper assembly, wherein, (i) when the rotatable yoke is rotating in the counter-clockwise direction and the stopper contacts the protruding portion, the rotatable yoke is prevented from further rotating in the counter-clockwise direction and (ii) when the rotatable yoke is rotating in the clockwise direction and the stopper contacts the protruding portion, the rotatable yoke is prevented from further rotating in the clockwise direction.

6. The pick and place device of claim 4, further comprising: a spring loaded stopper; and a protruding portion extending from the gripper assembly,
  wherein, (i) the rotatable yoke is prevented from further rotating in one of the clockwise direction or the counter-clockwise direction when the spring loaded stopper contacts the protruding portion and (ii) the rotatable yoke is free to further rotate continuously in the other of the clockwise direction or the counter-clockwise direction.

7. The pick and place device of claim 4, further comprising a one-way motion device configured to prevent the rotatable yoke from rotating in one of the clockwise direction or the counter-clockwise direction.

8. A pick and place device for use in an in vitro diagnostics automation system comprising:
  a motor;
  a rotatable motor shaft coupled to the motor and configured to rotate; and
  a gripping assembly comprising:
    a yoke selectively coupled to the rotatable motor shaft;
    a first movable finger mount having a first set of fingers extending therefrom and a second movable finger mount having a second set of fingers extending therefrom, the first movable finger mount and the second movable finger mount being coupled to the rotatable motor shaft;
    a first spring fixedly coupled between the yoke and the first movable finger mount, the first spring configured to apply a first inward force to the first movable finger mount toward the second movable finger mount in a linear direction; and
    a second spring fixedly coupled between the yoke and the second movable finger mount, the second spring configured to apply a second inward force to the second movable finger mount toward the first movable finger mount in the linear direction,
  wherein, the gripping assembly is configured to switch between:
  (i) a first state such that the rotation of the motor shaft causes the first movable finger mount and the first set of fingers to move in the linear direction toward and away from the second movable finger mount and the second set of fingers when the yoke is uncoupled from the rotatable motor shaft; and
  (ii) a second state such that the rotation of the motor shaft causes the yoke, the first movable finger mount, the second movable finger mount, the first set of fingers and the second set of fingers to rotate when the yoke is coupled to the rotatable motor shaft.

9. The pick and place device of claim 8, further comprising:
  a pinion coupled to the rotatable motor shaft and configured to rotate with the rotatable motor shaft;
  a first movable rack gear connected to the first movable finger mount and movably coupled to the pinion and configured to move the first movable finger mount in the linear direction when the pinion rotates; and
  a second movable rack gear connected to the second movable finger mount and movably coupled to the pinion and configured to move the second movable finger mount in the linear direction when the pinion rotates.

10. The pick and place device of claim 8, further comprising:
an encoder configured to generate a number of pulses per revolution of the gripping assembly motor when the encoder is moving with the rotatable motor shaft;
a home sensor configured to emit a beam; and
a home flag configured to block the beam of the home sensor and provide a home position of the gripping assembly.

11. The pick and place device of claim 8, wherein the rotatable yoke is further configured to rotate in a clockwise direction and a counter-clockwise direction with the rotatable motor shaft.

12. The pick and place device of claim 11, further comprising: a stopper; and
a protruding portion extending from the gripper assembly, wherein, (i) when the rotatable yoke is rotating in the counter-clockwise direction and the stopper contacts the protruding portion, the rotatable yoke is prevented from further rotating in the counter-clockwise direction; and (ii) when the rotatable yoke is rotating in the clockwise direction and the stopper contacts the protruding portion, the rotatable yoke is prevented from further rotating in the clockwise direction.

13. The pick and place device of claim 11, further comprising:
a spring loaded stopper; and
a protruding portion extending from the gripper assembly, wherein, (i) the rotatable yoke is prevented from further rotating in one of the clockwise direction or the counter-clockwise direction when the spring loaded stopper contacts the protruding portion and (ii) the rotatable yoke is free to further rotate continuously in the other of the clockwise direction or the counter-clockwise direction.

14. The pick and place device of claim 11, further comprising a one-way motion device configured to prevent the rotatable yoke from rotating in one of the clockwise direction or the counter-clockwise direction.

15. An in vitro diagnostics automation system comprising:
an analyzer having a track configured to provide one or more paths between testing stations of the analyzer;
a plurality of items to be transferred between different locations of the analyzer; and one or more pick and place devices each comprising:
a motor;
a rotatable motor shaft coupled to the motor and configured to rotate; and
a gripping assembly comprising:
a yoke selectively coupled to the rotatable motor shaft;
a first movable finger mount and a second movable finger mount, the first movable finger mount and the second movable finger mount being coupled to the rotatable motor shaft;
a first set of fingers extending from the first movable finger mount and a second set of fingers extending from the second movable finger mount;
a first spring fixedly coupled between the yoke and the first movable finger mount, the first spring configured to apply a first inward force to the first movable finger mount toward the second movable finger mount in the linear direction; and
a second spring fixedly coupled between the yoke and the second movable finger mount, the second spring configured to apply a second inward force to the second movable finger mount toward the first movable finger mount in the linear direction,
wherein the gripping assembly is configured to switch between:
(i) a first state such that the rotation of the motor shaft causes the first movable finger mount and the first set of fingers to move in a linear direction toward and away from the second movable finger mount and the second set of fingers to grip and release one or more of the plurality of items when the yoke is uncoupled from the rotatable motor shaft; and
(ii) a second state such that the rotation of the motor shaft causes the yoke, the first movable finger mount, the second movable finger mount, the first set of fingers and the second set of fingers to rotate in the rotational direction to orient one or more of the plurality of items when the yoke is coupled to the rotatable motor shaft.

16. The system of claim 15, wherein the yoke is further configured to rotate in a clockwise direction and a counter-clockwise direction with the rotatable motor shaft.

17. The system of claim 16, further comprising: a stopper; and
a protruding portion extending from the gripper assembly, wherein, (i) when the rotatable yoke is rotating in the counter-clockwise direction and the stopper contacts the protruding portion, the rotatable yoke is prevented from further rotating in the counter-clockwise direction and (ii) when the rotatable yoke is rotating in the clockwise direction and the stopper contacts the protruding portion, the rotatable yoke is prevented from further rotating in the clockwise direction.

18. The system of claim 16, further comprising: a spring loaded stopper; and
a protruding portion extending from the gripper assembly, wherein, (i) the rotatable yoke is prevented from further rotating in one of the clockwise direction or the counter-clockwise direction when the spring loaded stopper contacts the protruding portion and (ii) the rotatable yoke is free to further rotate continuously in the other of the clockwise direction or the counter-clockwise direction.

19. The system of claim 16, further comprising a one-way motion device configured to prevent the rotatable yoke from rotating in one of the clockwise direction or the counter-clockwise direction.

* * * * *